US008334363B2

(12) United States Patent
Hurd et al.

(10) Patent No.: US 8,334,363 B2
(45) Date of Patent: *Dec. 18, 2012

(54) OXIDIZED AND MALEATED COMPOUNDS AND COMPOSITIONS

(75) Inventors: Phillip W. Hurd, Conyers, GA (US); Gary D. Fultz, Spring, TX (US); Brett A. Neumann, Covington, GA (US); John B. Hines, Atlanta, GA (US)

(73) Assignee: Georgia-Pacific Chemicals LLC, Atlanta, GA (US)

( * ) Notice: Subject to any disclaimer, the term of this patent is extended or adjusted under 35 U.S.C. 154(b) by 139 days.

This patent is subject to a terminal disclaimer.

(21) Appl. No.: 12/023,886

(22) Filed: Jan. 31, 2008

(65) Prior Publication Data

US 2008/0194795 A1 Aug. 14, 2008

Related U.S. Application Data

(63) Continuation-in-part of application No. 11/669,713, filed on Jan. 31, 2007.

(51) Int. Cl.
*C09F 7/00* (2006.01)
*C11D 15/00* (2006.01)
(52) U.S. Cl. .......................... 530/230; 568/577; 568/664
(58) Field of Classification Search .................. 530/230; 568/577, 664
See application file for complete search history.

(56) References Cited

U.S. PATENT DOCUMENTS

| | | | | |
|---|---|---|---|---|
| 2,039,243 A * | 4/1936 | Krzikalla et al. | ............. | 530/214 |
| 2,551,436 A | 5/1951 | Hampton | | |
| 2,554,487 A | 5/1951 | Breslow | | |
| 2,569,404 A | 9/1951 | Dazzi | | |
| 2,569,405 A | 9/1951 | Dazzi | | |
| 2,569,406 A | 9/1951 | Dazzi | | |
| 2,569,407 A | 9/1951 | Dazzi | | |
| 2,569,420 A | 9/1951 | Kosmin | | |
| 2,598,634 A | 5/1952 | Dazzi | | |
| 2,627,514 A * | 2/1953 | Kirkpatrick et al. | .......... | 530/231 |
| 2,628,226 A | 2/1953 | Lawrence | | |
| 2,630,418 A | 3/1953 | Dazzi | | |
| 2,661,359 A | 12/1953 | Dazzi | | |
| 2,756,210 A | 7/1956 | Raifsnider | | |
| 2,776,277 A | 1/1957 | Keim | | |
| 3,043,786 A * | 7/1962 | White | .......................... | 521/43.5 |
| 3,106,550 A | 10/1963 | Bitting et al. | | |
| 3,112,209 A * | 11/1963 | Bradley, Jr. | .................... | 106/223 |
| 3,251,791 A * | 5/1966 | Goodchild | ................. | 525/501.5 |
| 3,278,562 A * | 10/1966 | Schnizer et al. | ............. | 549/528 |
| 3,341,485 A * | 9/1967 | Long | ............................... | 106/252 |
| 3,390,046 A | 6/1968 | McDavid | | |
| 3,497,490 A | 2/1970 | Arlt et al. | | |
| 3,522,279 A * | 7/1970 | Schnizer et al. | ............. | 549/272 |
| 3,632,822 A * | 1/1972 | Conroy | ......................... | 530/230 |
| 3,732,263 A * | 5/1973 | Berman | ........................ | 562/509 |
| 3,776,866 A | 12/1973 | Nakayama | | |
| 3,855,163 A * | 12/1974 | Bussell | .......................... | 530/230 |
| 3,919,453 A | 11/1975 | Bussell | | |
| 3,929,634 A | 12/1975 | Schuller | | |
| 3,931,336 A | 1/1976 | Schneider | | |
| 4,111,871 A * | 9/1978 | Aritomi | .......................... | 525/7.1 |
| 4,133,822 A * | 1/1979 | Hasman | ......................... | 530/230 |
| 4,207,231 A * | 6/1980 | Goodrich | ...................... | 524/705 |
| 4,218,851 A | 8/1980 | Rue | | |
| 4,233,162 A | 11/1980 | Carney | | |
| 4,292,221 A * | 9/1981 | Malatesta | ..................... | 524/313 |
| 4,312,631 A | 1/1982 | Cuntze et al. | | |
| 4,317,740 A * | 3/1982 | Eisenhard | ..................... | 508/238 |
| 4,337,193 A * | 6/1982 | Szita | ............................. | 527/105 |
| 4,410,431 A | 10/1983 | Roe | | |
| 4,415,337 A | 11/1983 | Kutta et al. | | |
| 4,447,344 A | 5/1984 | Roe | | |
| 4,511,366 A * | 4/1985 | Burrows et al. | ................. | 44/331 |
| 4,521,219 A * | 6/1985 | Perilstein | ........................ | 44/404 |
| 4,528,107 A | 7/1985 | McCaffrey et al. | | |
| 4,547,224 A | 10/1985 | Schilling | | |
| 4,614,235 A | 9/1986 | Keener et al. | | |
| 4,614,600 A | 9/1986 | Schilling et al. | | |
| 4,618,539 A * | 10/1986 | Jahnke et al. | ................. | 428/470 |
| 4,658,036 A | 4/1987 | Schilling | | |
| 4,751,025 A | 6/1988 | Olechowski et al. | | |
| 4,770,766 A | 9/1988 | Keller, Jr. et al. | | |
| 4,927,669 A | 5/1990 | Knox et al. | | |
| 4,957,511 A | 9/1990 | Ljusberg-Wahren | | |
| 5,147,528 A | 9/1992 | Bulatovic | | |
| 5,182,326 A | 1/1993 | LeBlanc et al. | | |
| 5,292,480 A | 3/1994 | Fischer et al. | | |
| 5,300,569 A * | 4/1994 | Drake et al. | .................... | 525/78 |
| 5,328,505 A | 7/1994 | Schilling | | |

(Continued)

FOREIGN PATENT DOCUMENTS

| | | |
|---|---|---|
| CA | 2 299 857 | 9/2000 |
| DE | 10015913 A1 * | 10/2000 |
| EP | 0 239 770 | 9/1989 |
| EP | 711850 | 5/1996 |
| EP | 1 676 897 | 7/2006 |
| JP | 18020 | 9/1949 |
| JP | 30-008548 | 11/1955 |
| JP | 32-000331 | 1/1957 |
| JP | 60-018583 | 1/1985 |
| WO | WO 89/11516 | 11/1989 |
| WO | WO 00/52230 | 9/2000 |
| WO | WO 2004/050801 | 6/2004 |
| WO | WO 2007/002558 | 1/2007 |

OTHER PUBLICATIONS

Machine translation DE 10015913 A1, 2010.*
Bickford et al. (Journal of the American Oil Chemists' Society, 1948, 254-257).*
Figge (Chem. Phys. Lipids 6 (1971) 164-182).*
Novakov, P. Iliev, I. et al., Synthesis and Properties of Some Epoxy Esters and Water-borne Coatings Prepared on their Basis, PRA Conference on Developments in New Technology and Marketing Opportunities in East and West Europe, Nov. 18-19, 1992, Brussels, Belgium.

(Continued)

*Primary Examiner* — Liam Heincer

(74) *Attorney, Agent, or Firm* — Ram W. Sabnis

(57) ABSTRACT

Oxidized and maleated compositions, such as oxidized and maleated tall oil compositions, can be prepared and used in a variety of industrial applications, including as emulsifiers and corrosion inhibitors.

10 Claims, 6 Drawing Sheets

U.S. PATENT DOCUMENTS

| | | | | |
|---|---|---|---|---|
| 5,338,347 A * | 8/1994 | Rohr et al. | | 106/14.44 |
| 5,344,483 A * | 9/1994 | Hinton | | 106/31.35 |
| 5,348,676 A * | 9/1994 | Takashima et al. | | 508/216 |
| 5,379,902 A | 1/1995 | Wen et al. | | |
| 5,385,616 A | 1/1995 | Dougherty et al. | | |
| 5,407,471 A * | 4/1995 | Rohr et al. | | 106/14.44 |
| 5,420,317 A * | 5/1995 | Laufenberg et al. | | 554/163 |
| 5,443,158 A | 8/1995 | McKenny et al. | | |
| 5,481,025 A * | 1/1996 | Laufenberg et al. | | 554/142 |
| 5,556,451 A | 9/1996 | Minevski | | |
| 5,582,792 A | 12/1996 | Dougherty et al. | | |
| 5,643,534 A | 7/1997 | Minevski | | |
| 5,658,860 A | 8/1997 | Clark et al. | | |
| 5,670,056 A | 9/1997 | Yoon et al. | | |
| 5,698,668 A * | 12/1997 | Bender | | 530/200 |
| 5,704,961 A | 1/1998 | Hudson | | |
| 5,759,485 A | 6/1998 | Fischer et al. | | |
| 5,795,376 A * | 8/1998 | Ide | | 106/31.73 |
| 5,864,049 A | 1/1999 | Dos Santos et al. | | |
| 5,869,433 A | 2/1999 | Patel | | |
| 5,929,408 A | 7/1999 | Gutierrez et al. | | |
| 5,977,037 A | 11/1999 | Giret et al. | | |
| 6,145,667 A | 11/2000 | Rothenberg et al. | | |
| 6,149,013 A | 11/2000 | Hughes | | |
| 6,153,693 A * | 11/2000 | Matzinger et al. | | 525/54.42 |
| 6,170,669 B1 | 1/2001 | Senior et al. | | |
| 6,200,377 B1 | 3/2001 | Basilio et al. | | |
| 6,341,697 B1 | 1/2002 | Miller et al. | | |
| 6,375,853 B1 | 4/2002 | Yoon | | |
| 6,409,022 B1 | 6/2002 | Rothenberg et al. | | |
| 6,426,321 B1 | 7/2002 | Durrieu et al. | | |
| 6,469,125 B1 * | 10/2002 | Fontana et al. | | 528/158.5 |
| 6,526,675 B1 | 3/2003 | Yoon | | |
| 6,583,263 B2 | 6/2003 | Gaudl | | |
| 6,589,917 B2 | 7/2003 | Patel et al. | | |
| 6,620,770 B1 | 9/2003 | Kirsner et al. | | |
| 6,666,268 B2 | 12/2003 | Griffith et al. | | |
| 6,668,929 B2 | 12/2003 | Griffith et al. | | |
| 6,774,094 B2 | 8/2004 | Jovancicevic et al. | | |
| 6,793,079 B2 | 9/2004 | Khan et al. | | |
| 6,799,682 B1 | 10/2004 | Yoon | | |
| 6,800,594 B2 | 10/2004 | Miksic et al. | | |
| 6,849,581 B1 | 2/2005 | Thompson et al. | | |
| 6,871,743 B2 | 3/2005 | Yoon | | |
| 6,988,623 B2 | 1/2006 | Magliocco et al. | | |
| 7,008,907 B2 | 3/2006 | Kirsner et al. | | |
| 7,137,401 B2 | 11/2006 | Jovancicevic et al. | | |
| 7,479,184 B1 * | 1/2009 | Dehuvyne et al. | | 106/218 |
| 2003/0116065 A1 | 6/2003 | Griffith et al. | | |
| 2003/0130135 A1 | 7/2003 | Hou et al. | | |
| 2004/0144957 A1 | 7/2004 | Miksic et al. | | |
| 2004/0171498 A1 | 9/2004 | Miller | | |
| 2005/0080178 A1 | 4/2005 | Fujii et al. | | |
| 2005/0137093 A1 | 6/2005 | Miller | | |
| 2007/0075120 A1 * | 4/2007 | Yang et al. | | 228/101 |
| 2007/0167333 A1 * | 7/2007 | Hurd et al. | | 507/244 |
| 2008/0179570 A1 * | 7/2008 | Hurd et al. | | 252/396 |
| 2008/0272342 A1 | 11/2008 | Guzmann et al. | | |
| 2008/0305531 A1 * | 12/2008 | Lam et al. | | 435/142 |
| 2009/0065736 A1 * | 3/2009 | Johnson et al. | | 252/88.1 |
| 2009/0194466 A1 * | 8/2009 | Hines et al. | | 209/166 |
| 2009/0194731 A1 | 8/2009 | Hurd et al. | | |
| 2010/0028272 A1 | 2/2010 | Knappe et al. | | |

OTHER PUBLICATIONS

SciFinder Search Results for "Maleated Tall Oil, Oxidized." Search conducted Aug. 25, 2006 yielding four references. pp. 1-3.
SciFinder Search Results for "Oxidized Maleated Tall Oil." Search conducted Aug. 25, 2006 yielding four references. pp. 1-3.
Specification for Tall Oil Products—Product Information "XTOL® 690 Modified Tall Oil." 1996, 2002 Georgia-Pacific Resins, Inc.
Specification for Tall Oil Products—Product Information "Latol MTO® Oxidized Tall Oil." 1996, 2002 Georgia-Pacific Resins, Inc.
Specification for Tall Oil Products—Product Information "XTOL® 304 Tall Oil Fatty Acid." 1996, 2002, 2007 Georgia-Pacific Chemicals LLC.
Specification for Tall Oil Products—Product Information "XTOL® 100 Tall Oil Fatty Acid." 1996, 2002, 2007 Georgia-Pacific Chemicals LLC.
Specification for Tall Oil Products—Product Information "XTOL® 101 Tall Oil Fatty Acid." 1996, 2002, 2007 Georgia-Pacific Chemicals LLC.
Specification for Tall Oil Products—Product Information "XTOL® 300 Tall Oil Fatty Acid." 1996, 2002, 2007 Georgia-Pacific Chemicals LLC.
Specification for Tall Oil Products—Product Information "XTOL® 531 Distilled Tall Oil." 1996, 2002 Georgia-Pacific Resins, Inc.
Material Safety Data Sheet—"XTOL® 692 Modified Tall Oil." pp. 1-6. Effective Date May 23, 2005. Georgia-Pacific Chemicals LLC.
Novakov et al., "Synthesis and properties of some epoxy esters and water-borne coatings prepared on their basis," *Surface Coatings International*, 1993, 76(3):111-115.
Isogai et al., "Emulsion stability and sizing performance of alkyl oleate-succinic anhydrides," *Paper Technology*, 2004, 45(7):19-24.
Izumi et al., "Fatty acid derivatives and their utilization. IX. Synthesis and properties of high-molecular-weight aliphatic poly(arnide-amines)," *Kogyo Kagaku Zasshi*, 1969, 72(4):1018-1022 (includes English summary).
Eslami, "Addition products of maleic anhydride with oleic acid and some of their derivatives," *J. Rech. Centre Natl. Rech. Sci.*, Lab Bellevue (Paris), 1962, No. 61, pp. 333-355 (includes English summary).
Shigeno et al., "Derivatives of maleinated monoolefinic unsaturated fatty acids as synthetic lubricants and oiliness improver," *Kogyo Kagaku Zasshi*, 1957, 60:582-586 (includes English summary).
Shigeno et al., "trans-Stereoisomer of adducts of maleic anhydride with olefinic unsaturated fatty acids," *Kogyo Kagaku Zasshi*, 1957, 60:577-582 (includes English summary).
Shigeno et al., "Derivatives of maleinated monoolefinic unsaturated fatty acids and their utilization as rust inhibitor, antibacterial agent, surface-active agent, and stabilizer for poly(vinyl chloride) resin," *Kogyo Kagaku Zasshi*, 1957, 60:720-728 (includes English summary).
Volodkovich et al., "Organic insectofungicides. XXXV. Reaction of 1,1-difluorotetrachlorocyclopentadiene with some unsaturated compounds," *Zhurnal Obshchei Khimmii*, 1958, 28(10):3123-3126 (English translation).
G.F. Filippychev et al., Khim. Him. Teckhnol., 1973, 25-27 Novakov, P. et al., Surface Coatings International, 76 (3):111-115(1993).
Babkina, M.M. et al., "Alkyl Resins Made from Tall Oil and Maleic Anhydride", Deposited Doc. (1980), 12 pp.
Material Safety Data Sheet—"XTOL® 0530 Rosin Fortified Distilled Tall Oil", pp. 1-6, Effective Date Oct. 30, 1997, Georgia Pacific Chemicals LLC.
Material Safety Data Sheet—"LYTOR® 100 Tall Oil Rosin", pp. 1-7, Effective Date Jan. 22, 2001, Georgia-Pacific Chemicals LLC.
Material Safety Data Sheet—"LYTOR® 101 Tall Oil Rosin", pp. 1-7, Effective Date Jan. 22, 2001, Georgia-Pacific Chemicals LLC.
Material Safety Data Sheet—"XTOL® 0520 Distilled Tall Oil", pp. 1-7, Effective Date Dec. 9, 2004, Georgia-Pacific Chemicals LLC.
Material Safety Data Sheet—"XTOL® MTO Modified Tall Oil", pp. 1-7, Effective Date May 23, 2007, Georgia-Pacific Chemicals LLC.
Material Safety Data Sheet—"XTOL® 0542 Rosin Fortified Distilled Tall Oil", pp. 1-7, Effective Date Oct. 9, 2007, Georgia-Pacific Chemicals LLC.
Material Safety Data Sheet—"XTOL® 692 Modified Tall Oil", pp. 1-7, Effective Date Oct. 30, 2007, Georgia-Pacific Chemicals LLC.
Material Safety Data Sheet—"XTOL® 690 Modified Tall Oil", pp. 1-7, Effective Date Jan. 23, 2008, Georgia-Pacific Chemicals LLC.
Material Safety Data Sheet—"XTOL® 304 Tall Oil Fatty Acids", pp. 1-6, Effective Date Apr. 4, 2008, Georgia-Pacific Chemicals LLC.
Material Safety Data Sheet—"XTOL® 100 Tall Oil Fatty Acids", pp. 1-6, Effective Date Apr. 14, 2008, Georgia-Pacific Chemicals LLC.
Material Safety Data Sheet—"XTOL® 101 Tall Oil Fatty Acids", pp. 1-6, Effective Date Apr. 14, 2008, Georgia-Pacific Chemicals LLC.
Material Safety Data Sheet—"XTOL® 300 Tall Oil Fatty Acids", pp. 1-6, Effective Date Apr. 14, 2008, Georgia-Pacific Chemicals LLC.

Huntsman Corporation, Technical Bulletin for "JEFFAMINE® D-230 amine Epoxy Curing Agent", 1 page, 2005, 2006.

Huntsman Corporation, Technical Bulletin for "JEFFAMINE® D-400 Polyetheramine", 2 pages, 2007, 2008.

Huntsman Corporation, Technical Bulletin for "JEFFAMINE® D-2000 Polyetheramine", 2 pages, 2007, 2008.

Kantro, D.L. "Influence of Water-Reducing Admixtures on Properties of Cement Paste—A Miniature Slump Test", Cement, Concrete, and Aggregates, vol. 2, No. 2, Winter 1980, pp. 95-102, ASTM International.

Shi, et al., Functionalization of Isotactic Polyproplylene with Maleic Anhydride by Reactive Extrusion: Mechanism of Melt Grating, Polymer, vol. 42, 2001, pp. 5549-5557. Elsevier Science Limited.

International Search and Written Opinion of the International Search Authority for PCT/US2009/032701 mailed May 20, 2009.

Office Actions for U.S. Appl. No. 11/669,713, 2011.

Office Actions for U.S. Appl. No. 12/363,483, 2010.

* cited by examiner

OXIDIZED AND MALEATED COMPOUNDS AND COMPOSITIONS

CROSS-REFERENCE TO RELATED APPLICATIONS

This application is a continuation-in-part of U.S. application Ser. No. 11/669,713 filed on Jan. 31, 2007, which is incorporated by reference in its entirety herein.

TECHNICAL FIELD

This disclosure relates to compounds, which are both oxidized and maleated, and methods of making and using such compounds. This disclosure also relates to compositions, which include oxidized and maleated compounds, and methods of making and using such compositions.

BACKGROUND

Tall oil is a mixture of mainly acidic compounds found in pine trees and obtained as a by-product of the pulp and paper industry. It is produced, for example, in the form of a resinous yellow-black oily liquid as an acidified byproduct in the Kraft or sulfate processing of pine wood. Tall oil, also known as "tallol" or "liquid resin", prior to refining, is normally a mixture of rosin acids, fatty acids, sterols, high-molecular weight alcohols, and other alkyl chain materials (i.e. rosin acids, fatty acids, and unsaponifiables or "neutral compounds"). Distillation of crude tall oil can be used to recover a mixture of fatty acids in the $C_{16-20}$ range. Commercially available tall oil products XTOL® 100, XTOL® 300, and XTOL® 304 (all from Georgia-Pacific Chemicals LLC, Atlanta, Ga.), for example, all contain saturated and unsaturated fatty acids in the $C_{16-20}$ range, as well as minor amounts of rosin acids. It should be appreciated that, as tall oil is derived from a natural source, its composition can vary. The main fatty acids found in all tall oils, however, are oleic, linoleic, stearic, and palmitic acids.

Tall oil has a variety of uses in industry. For example, it can be used as a frothing agent in the flotation process for reclaiming low grade copper-, lead-, and zinc-bearing ores, and as a solvent or wetting agent in a variety of textile and synthetic fiber manufacturing processes. The distilled fatty acids can be used in soaps, detergents, and disinfectants and as a base for lubricating greases, textile oils, cutting oils, and metal polishes. Rosin acids can be used in rubber polymerization and compounding, as size to impart water resistance to paper, and in adhesives and printing inks.

SUMMARY

This disclosure provides compositions comprising compounds, which compounds are both maleated and oxidized. In some embodiments, the maleated and oxidized compounds are dimer-type acids based on fatty acids, rosin acids, or mixtures thereof. In some embodiments, the maleated and oxidized compounds are trimer-type acids based on fatty acids, rosin acids, or mixtures thereof. In some embodiments, the fatty acids, rosin acids, or mixtures thereof are derived from tall oil, vegetable oil, animal oil, algal produced oil, microbial produced oil, or mixtures thereof.

This disclosure also provides methods of making compositions comprising maleated and oxidized compounds. In some embodiments, the compositions are made by oxidizing and maleating a source of fatty acids, rosin acids, or mixtures thereof. In some embodiments, the source of fatty acids, rosin acids, or mixtures thereof is a tall oil, a vegetable oil, an animal oil, algal produced oil, microbial produced oil, or mixtures thereof.

This disclosure also provides methods of using oxidized and maleated compounds and compositions. In some methods, compounds and compositions in accordance with some embodiments of the invention can be used as emulsifiers. In some methods, compounds and compositions in accordance with some embodiments of the invention can be used as corrosion inhibitors.

Provided herein is an oxidized and maleated composition. In some embodiments, the composition comprises one or more of: oxidized and maleated decenoic acid; oxidized and maleated dodecenoic acid; oxidized and maleated cis-9-tetradecenoic acid; oxidized and maleated cis-9-hexadecenoic acid; oxidized and maleated oleic acid; oxidized and maleated linoleic acid; oxidized and maleated linolenic acid; oxidized and maleated cis-6,cis-9,cis-12,cis-15-octadecatetraenoic acid; oxidized and maleated ricinoleic acid; oxidized and maleated cis-9-eicosenoic acid; oxidized and maleated cis-11-eicosenoic acid; oxidized and maleated eicosadienoic acid; oxidized and maleated eicosatrienoic acid; oxidized and maleated arachidonic acid; oxidized and maleated eicosapentaenoic acid; oxidized and maleated erucic acid; oxidized and maleated docosadienoic acid; oxidized and maleated 4,8,12,15,19-docosapentaenoic acid; oxidized and maleated docosahexaenoic acid; and oxidized and maleated tetracosenoic acid.

In some embodiments, the composition has an acid value from about 50 to about 400 mg KOH/g. In some embodiments, the composition has a viscosity of about 1,000 to about 27,000 cPs at 25° C.

In certain embodiments, the composition is an oxidized and maleated tall oil composition. The oxidized and maleated tall oil composition comprises one or more oxidized and maleated fatty acids, rosin acids, or combinations thereof. In some embodiments, the oxidized and maleated tall oil composition is chosen from crude tall oil; tall oil fatty acid; and tall oil distillation bottoms. In certain embodiments, the oxidized and maleated tall oil composition comprises compounds having at least three acid functionalities. In other embodiments, the oxidized and maleated tall oil composition comprises compounds having at least six acid functionalities.

Also provided herein is a tall oil composition comprising compounds having at least three acid functionalities. In some embodiments, the composition comprises compounds having at least six acid functionalities. The tall oil composition comprises one or more oxidized and maleated fatty acids, rosin acids, or combinations thereof. In some embodiments, the tall oil composition further comprises one or more of free fatty acid, rosin acid, maleated but not oxidized fatty acid, maleated but not oxidized rosin acid, oxidized but not maleated fatty acid, oxidized but not maleated rosin acid, oxidized and partially maleated fatty acid, and oxidized and partially maleated rosin acid.

In certain embodiments, the tall oil composition comprises one or more of the following:

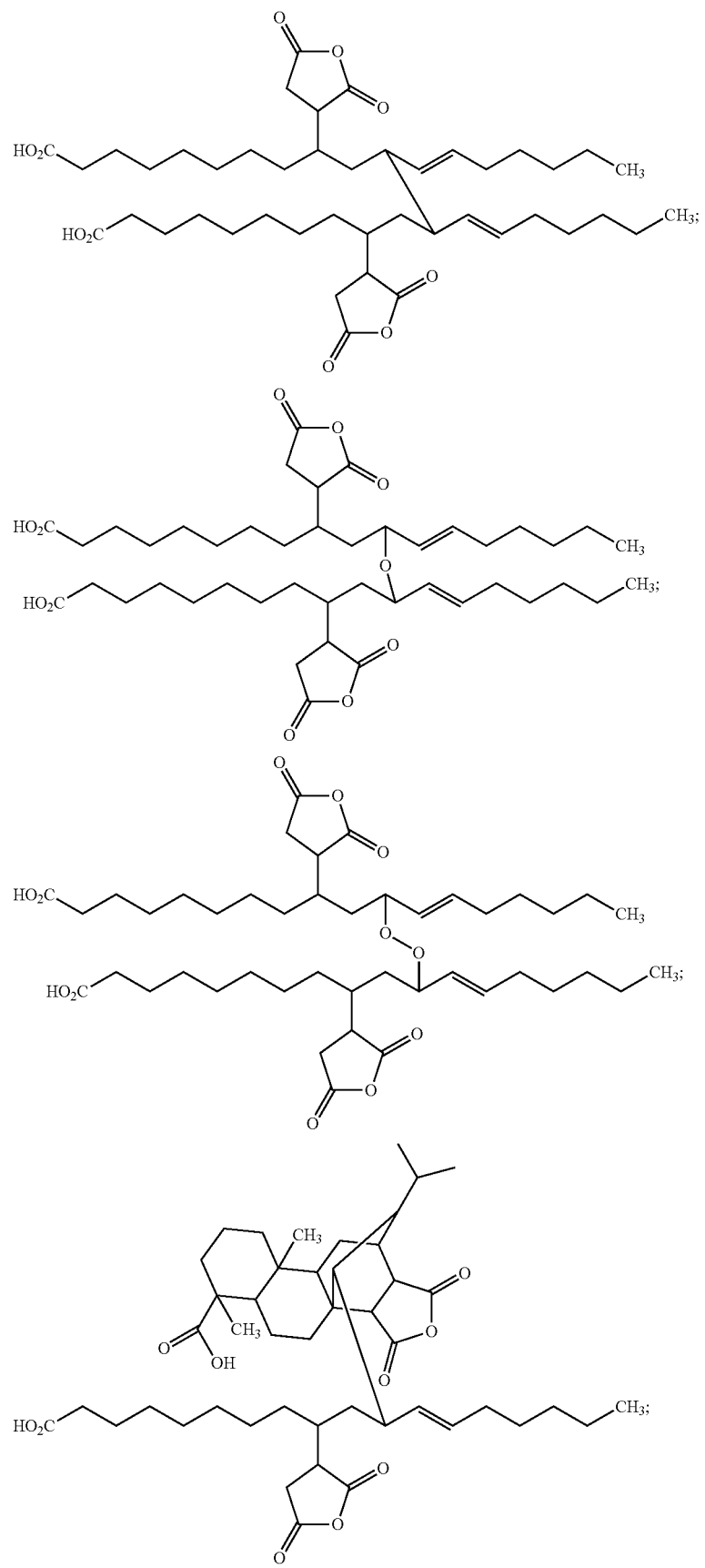

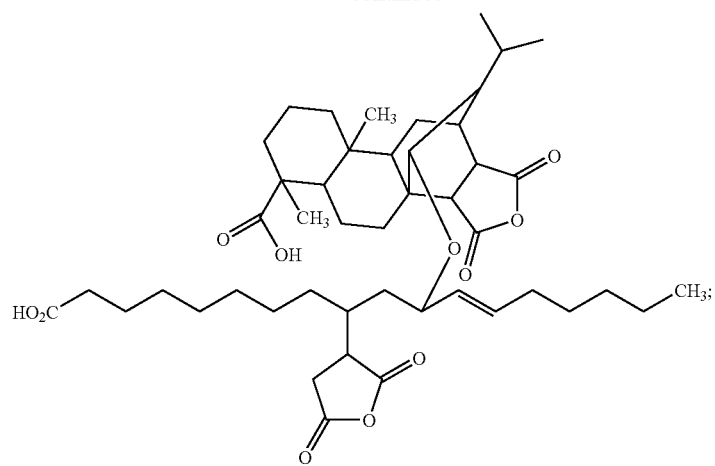
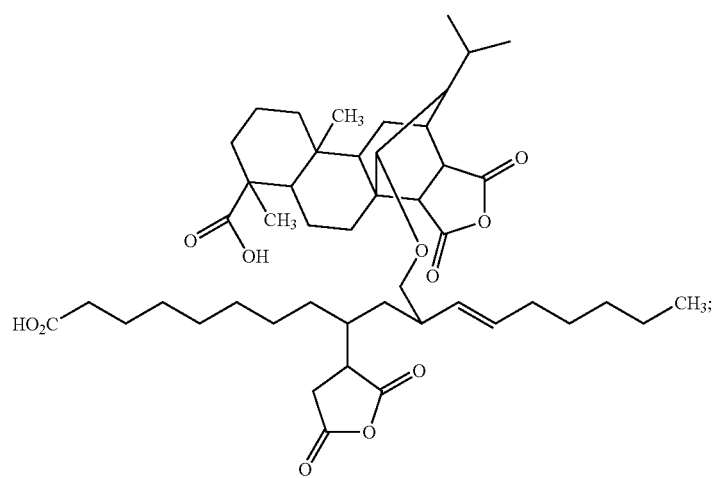
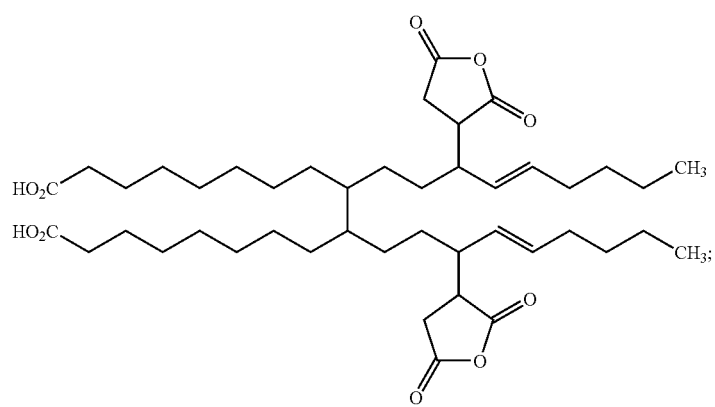

-continued
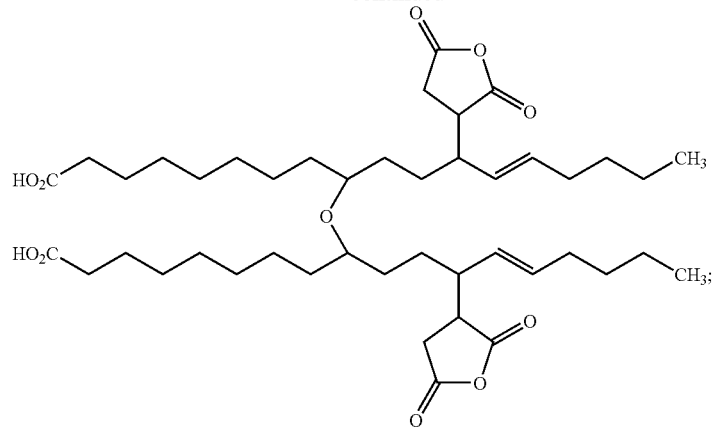
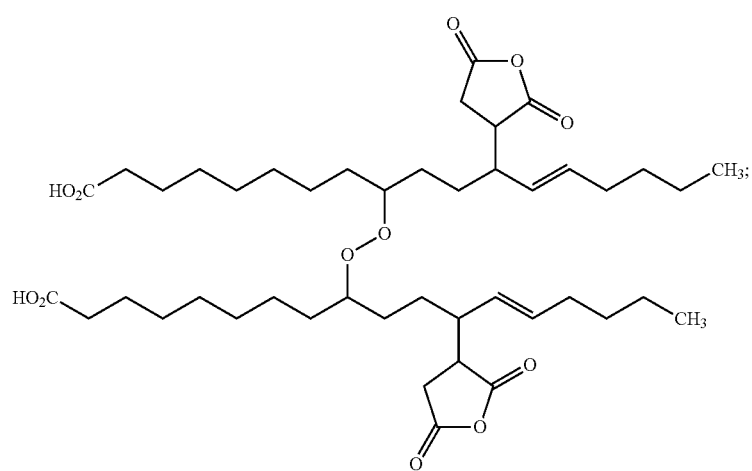
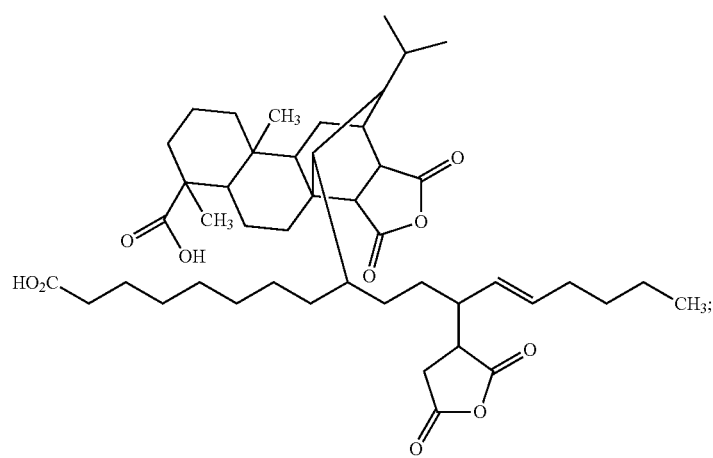

-continued
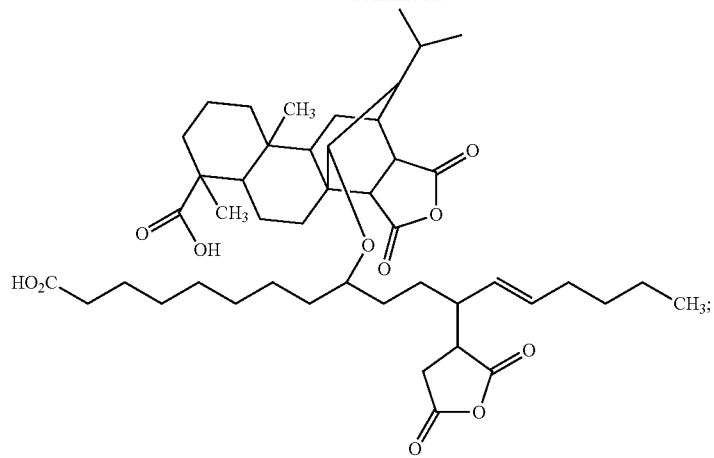
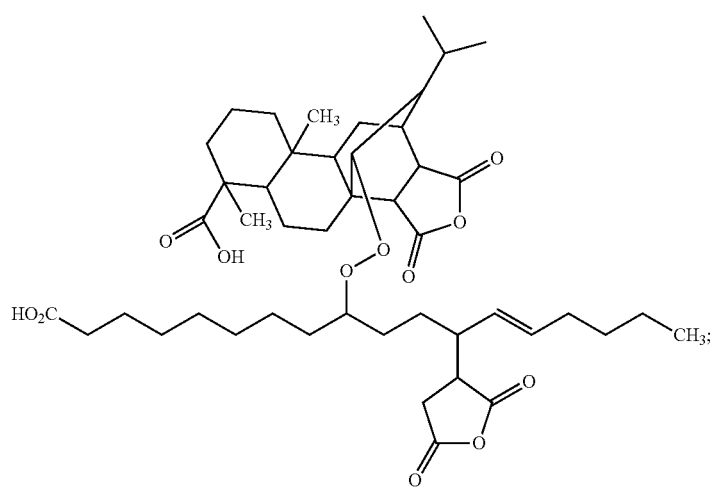
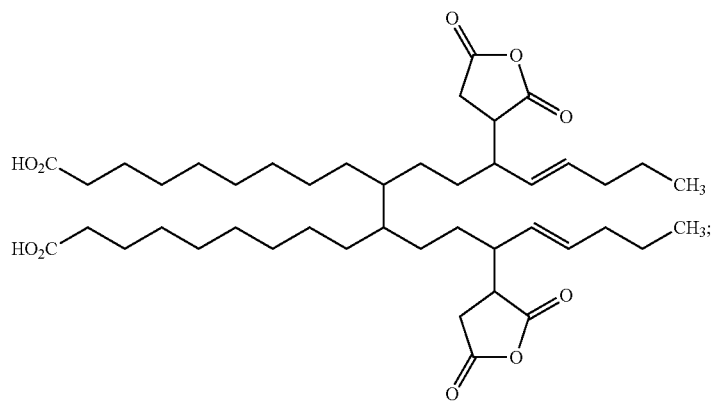

-continued
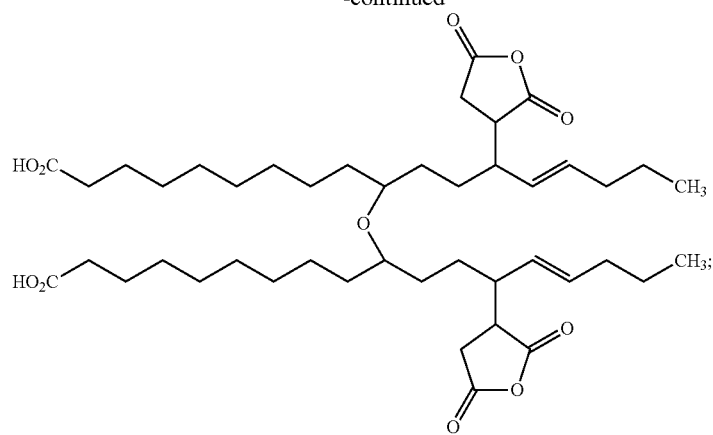
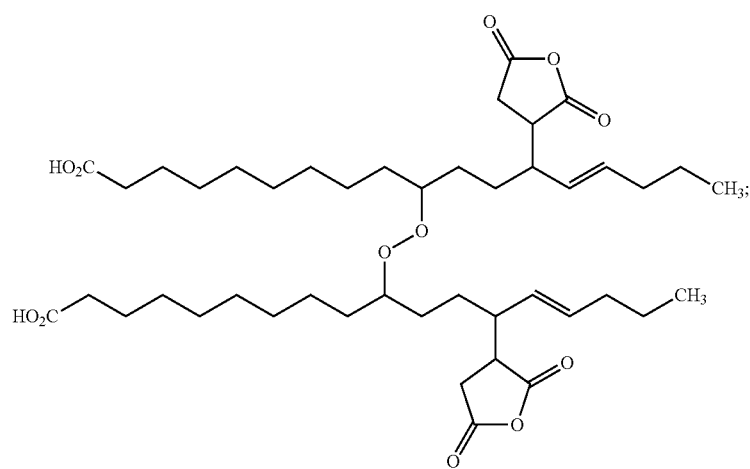
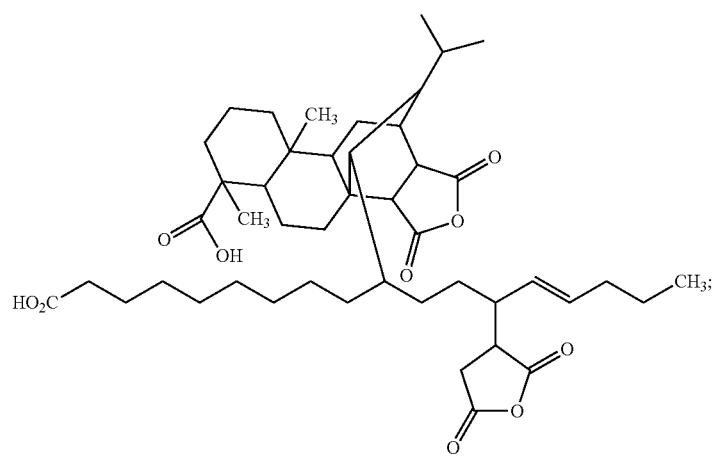

-continued
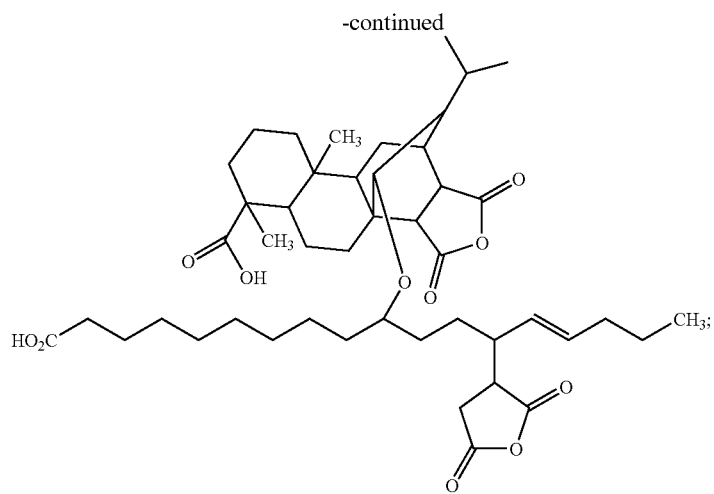
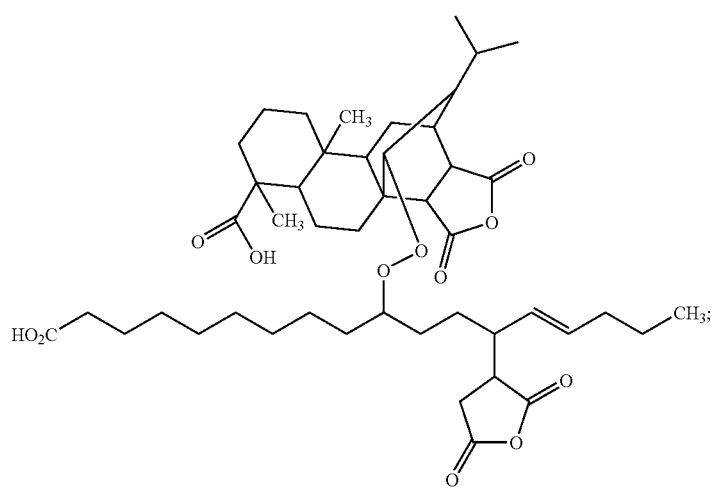
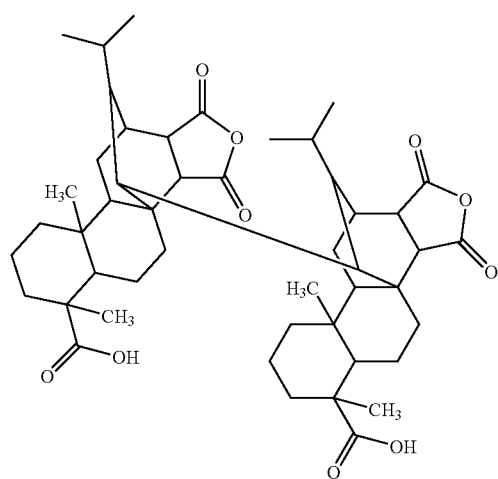

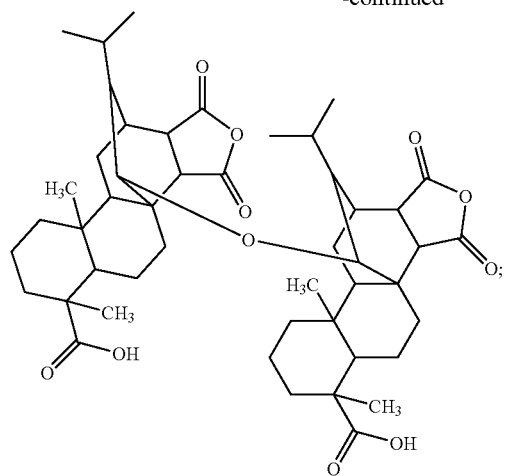
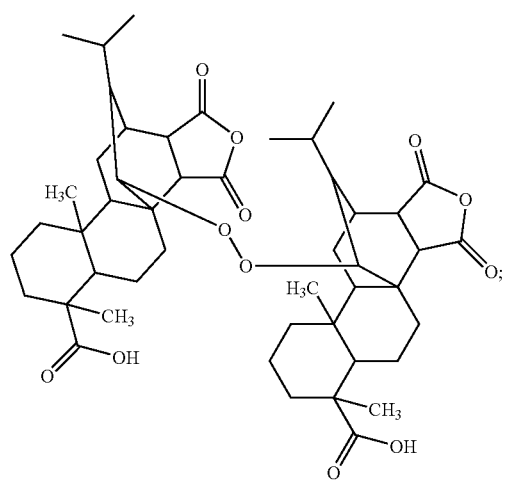
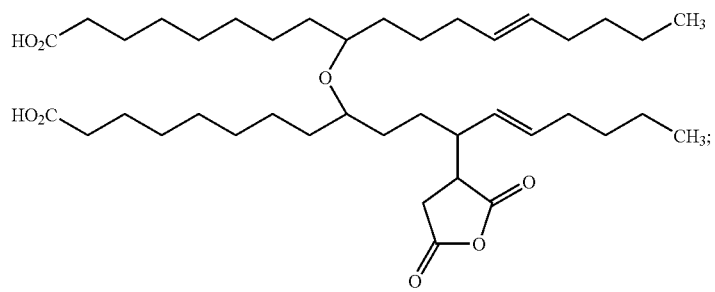
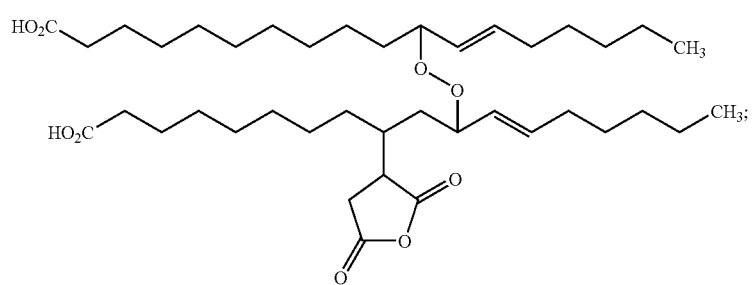

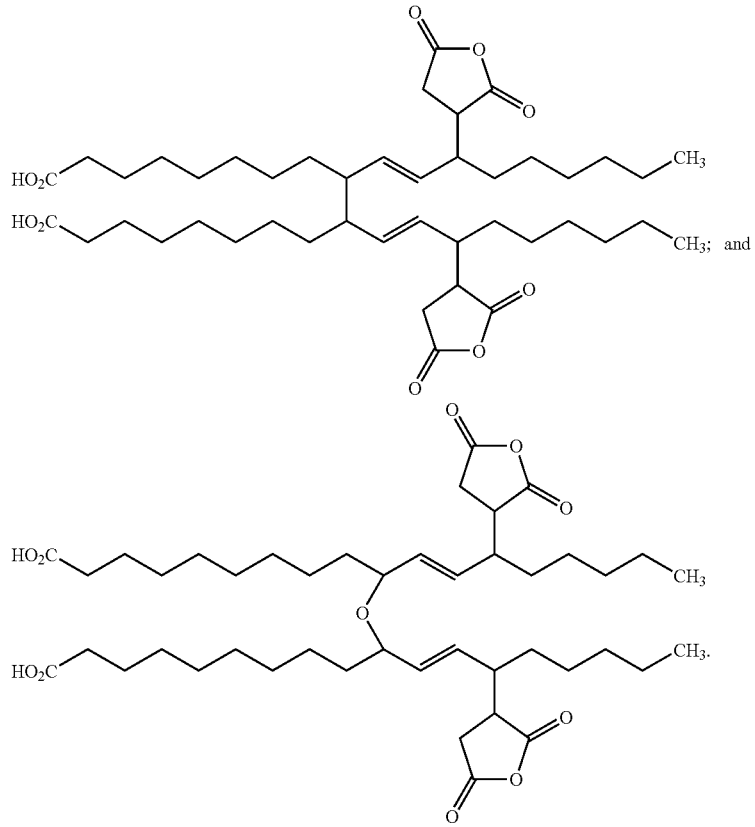

Further provided herein is a composition comprising a compound of formula I:

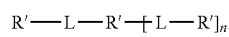

wherein L is chosen from a direct bond, —O—, or —OO—; n is 0 or 1; and R' is a compound of formula II:

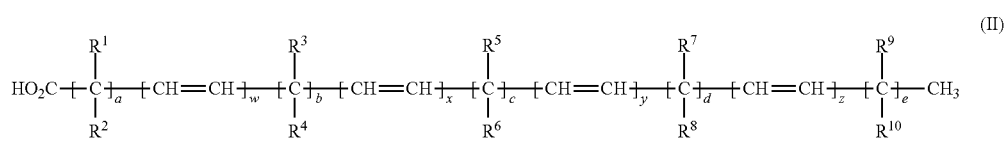

wherein a, b, c, d, and e are each independently a number from 0 to 20; w, x, y, and z are each independently 0 or 1; $R^1$-$R^{10}$ are each independently chosen from L, H, alkyl, alkenyl, alkynyl, alkoxy, amino, hydroxy,

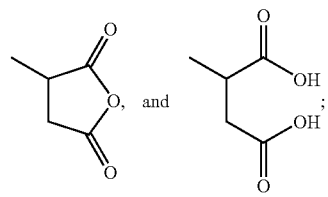

and wherein at least one of $R^1$-$R^{10}$ is L; wherein the sum of a, b, c, d, e, w, x, y, and z is a number from 8 to 22; and wherein at least one of w, x, y, and z is 1; and wherein the compound of Formula I comprises at least one R' wherein at least one of $R^1$-$R^{10}$ is

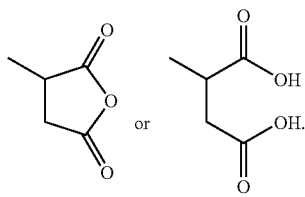

In some embodiments, the sum of a, b, c, d, e, w, x, y, and z is 16. In certain embodiments, the compound has at least three acid functionalities. In other embodiments, the composition has an acid value from about 50 to about 400 mg KOH/g. In some embodiments, the composition has a viscosity of about 1000 to about 27,000 cPs at 25° C.
In some embodiments, the compound of formula I is chosen from:
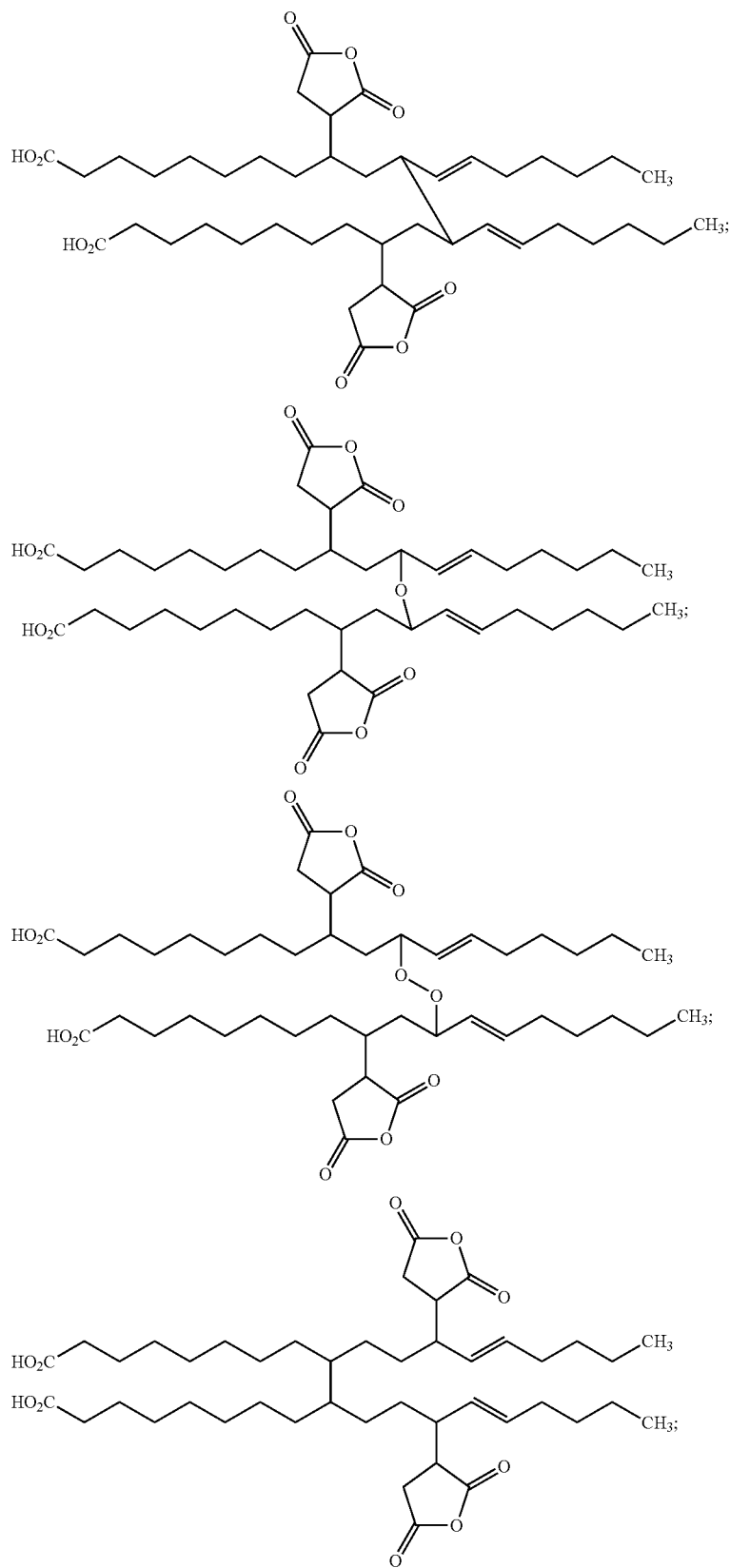

-continued
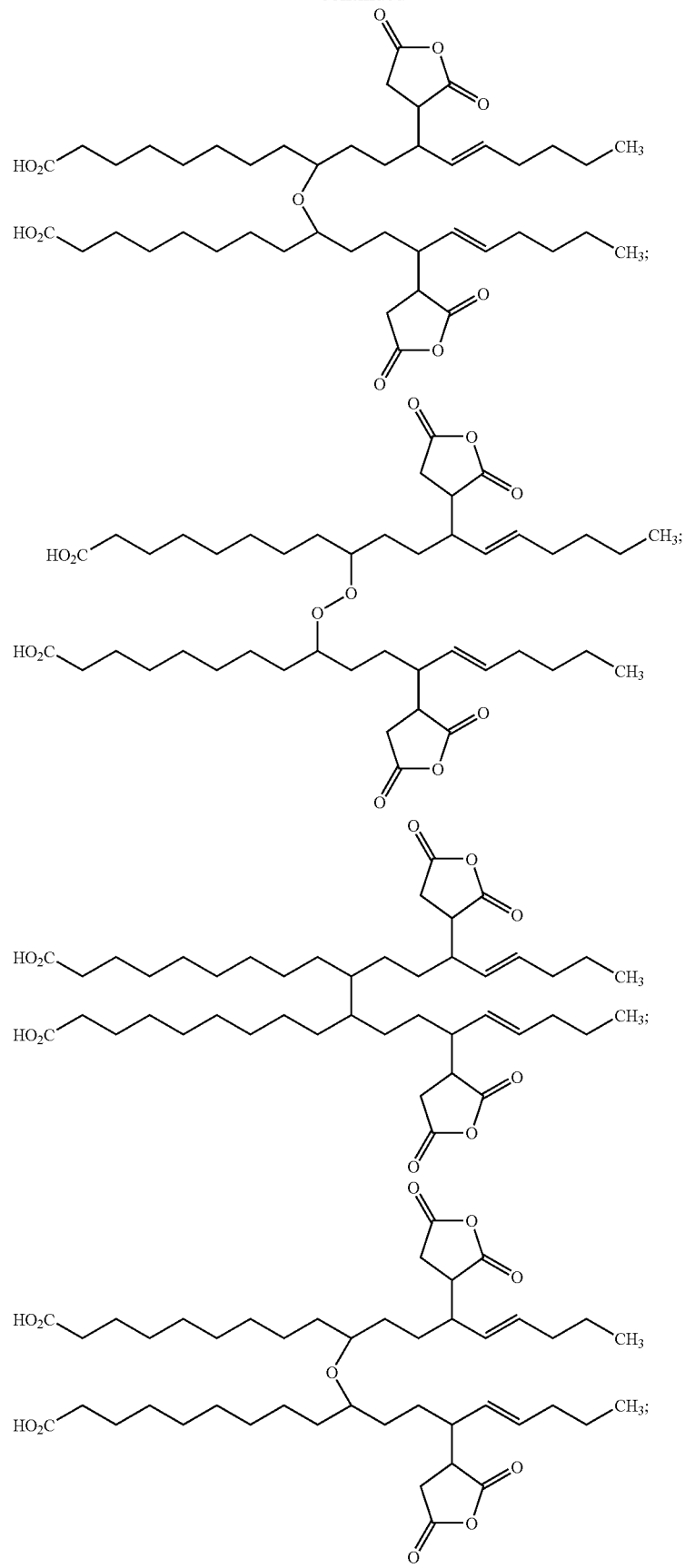

-continued
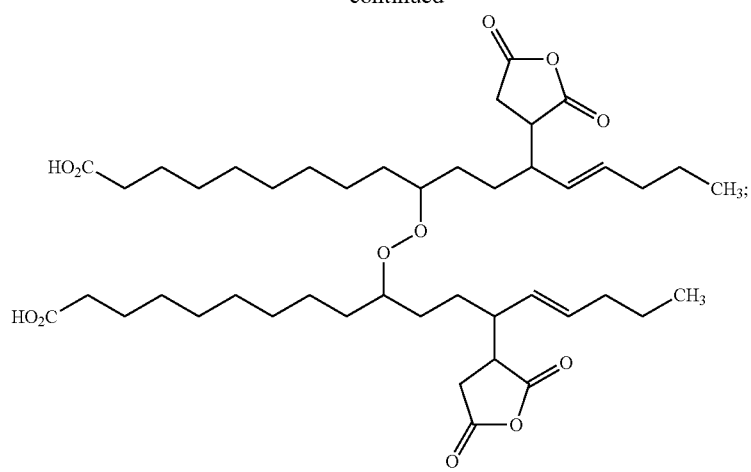
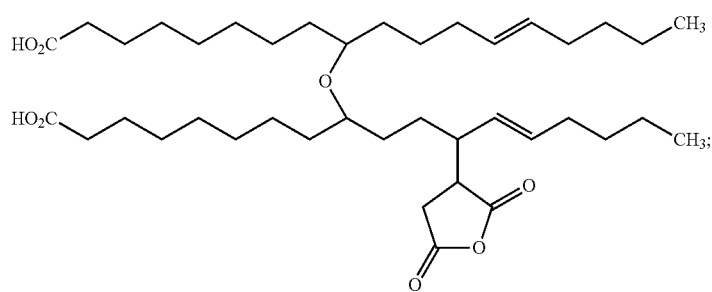
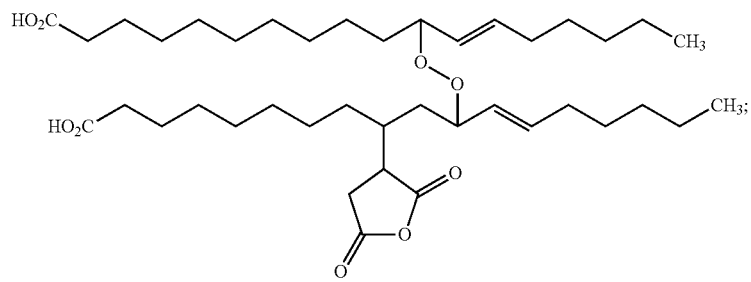
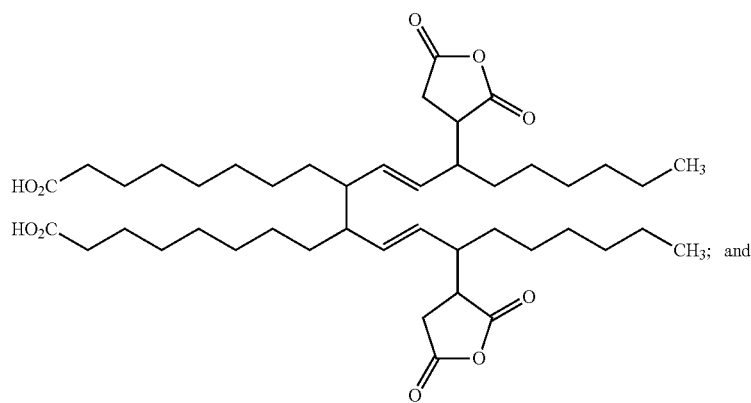

-continued

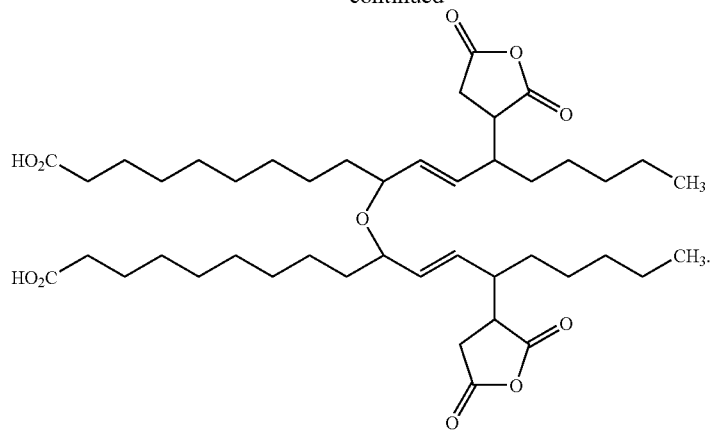

Also provided herein is a composition, comprising: a compound of formula I:

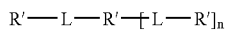

wherein L is chosen from a direct bond, —O—, or —OO—; n is a number chosen from 0, 1, 2, 3, 4, and 5; and R' is a compound of formula II:

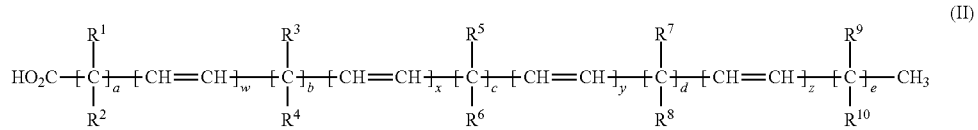

wherein a, b, c, d, and e are each independently a number from 0 to 20; w, x, y, and z are each independently 0 or 1; $R^1$-$R^{10}$ are each independently chosen from L, H, alkyl, alkenyl, alkynyl, alkoxy, amino, hydroxy, and X; and wherein at least one of $R^1$-$R^{10}$ is L;

wherein X is an α,β unsaturated carboxylic acid or anhydride; wherein the sum of a, b, c, d, e, w, x, y, and z is a number from 8 to 22; and wherein at least one of w, x, y, and z is 1; and wherein the compound of Formula I comprises at least one R' wherein at least one of $R^1$-$R^{10}$ is X.

Further provided herein is a product produced by the process of oxidizing and maleating a composition comprising a hydrocarbon-based backbone structure having at least one site of unsaturation, such as an unsaturated fatty acid. In some embodiments, the composition is oxidized and then maleated. In other embodiments, the composition is maleated and then oxidized. In certain embodiments, the composition is a plant-based oil, animal-based oil, algal produced oil, or microbial produced oil. In some embodiments, the plant- or animal-based oil is chosen from: canola oil; castor oil; coco butter; coconut oil; corn oil; cotton seed oil; crambe oil; linseed oil; olive oil; palm kernel oil; palm oil; peanut oil; rape seed oil; safflower oil; soybean oil; sunflower oil; tall oil; butter; lard; tallow; yellow grease; and fish oil.

A method of preparing an oxidized and maleated composition is provided herein. The method comprises: (a) providing a composition comprising one or more of a hydrocarbon-based backbone structure having at least one site of unsaturation, such as an unsaturated fatty acids, rosin acid, or mixtures thereof; (b) maleating the composition; and (c) oxidizing the composition. In some embodiments, the composition is chosen from crude tall oil; tall oil fatty acid; and tall oil distillation bottoms.

Further provided herein are methods of using oxidized and maleated compositions. In one embodiments a method of emulsifying a solution is described, the method comprising combining the solution with an effective amount of an oxidized and maleated composition. In another embodiments, a method of inhibiting corrosion on a metal surface is provided, the method comprising contacting the metal surface with an effective amount of an oxidized and maleated composition. In some embodiments, a method of reducing corrosion on a metal surface is provided, the method comprising contacting the metal surface with an effective amount of an oxidized and maleated composition.

The details of one or more non-limiting embodiments of the invention are set forth in the accompanying drawings and the description below. Other embodiments of the invention should be apparent to those of ordinary skill in the art after consideration of the present disclosure.

DETAILED DESCRIPTION

I. Definitions

Figure 1:
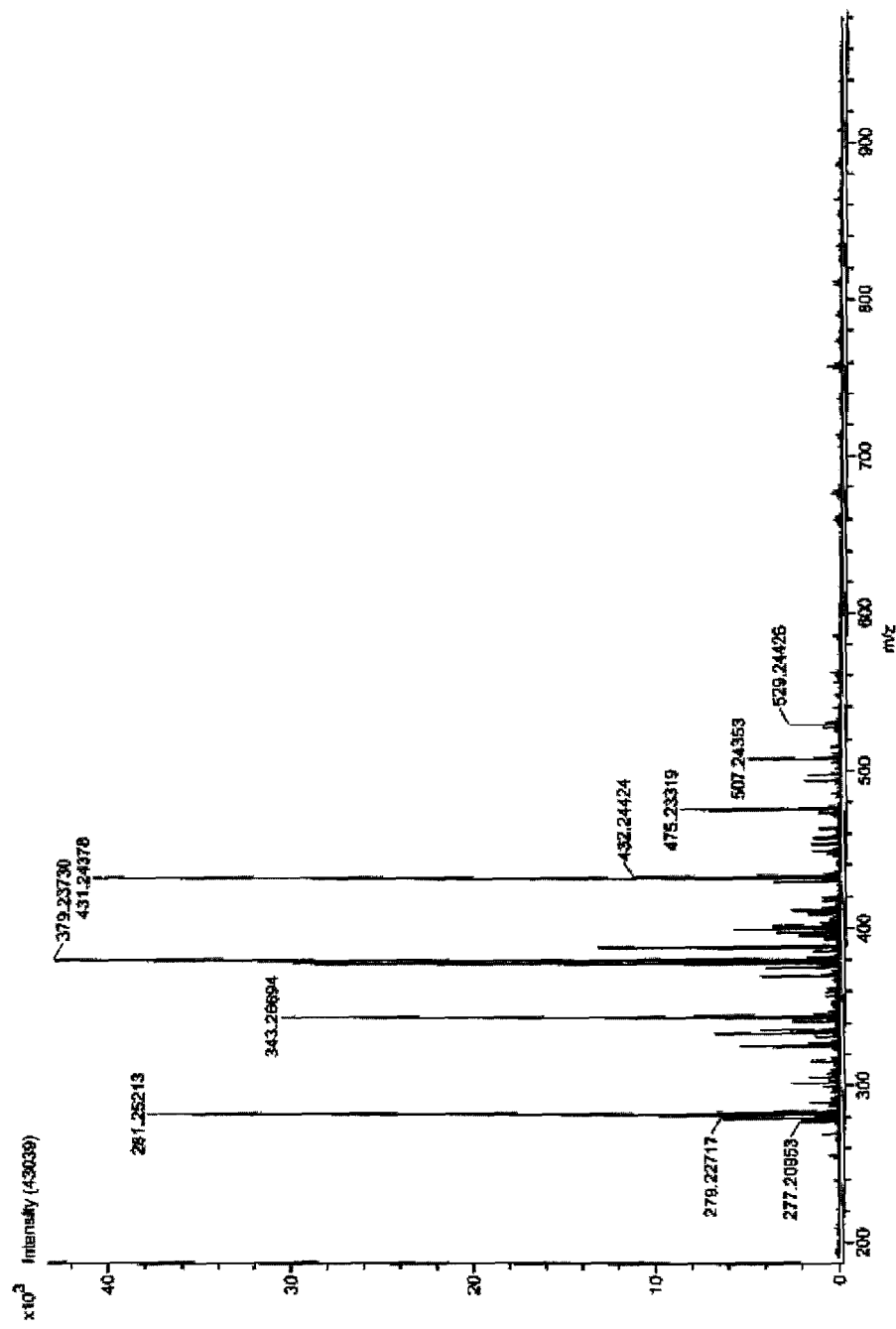
FIG. 1 is a time-of-flight mass spectrum of an oxidized and maleated TOFA.

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

An "oxidized and maleated compound" (hereinafter an "oxmal compound") is a compound, or salt thereof, comprising at least two or more hydrocarbon-based backbone structures, wherein at least one of the backbone structures is substituted by at least one of an α,β unsaturated carboxylic acid or anhydride, and further wherein each backbone structure is linked to one other backbone structure by a bridging group chosen from a direct bond, an ether linkage, or a peroxide linkage located at a non-terminal position of each backbone structure. In some embodiments, the hydrocarbon-based backbone structure is a $C_{10}$-$C_{24}$ hydrocarbon. In some embodiments, the hydrocarbon-based backbone is a $C_{10}$-$C_{24}$ fatty acid or rosin acid. In some embodiments, the α,β unsaturated carboxylic acid or anhydride is maleic anhydride, fumaric acid, acrylic acid, or methacrylic acid (herein acrylic acid and methacrylic acid are generally referred to in the aggregate or alternative as (meth)acrylic acid). In some embodiments, the α,β unsaturated carboxylic acid or anhydride is a biogenically derived unsaturated carboxylic acid or anhydride. Non-limiting examples of oxmal compounds include dimers and trimers of fatty acids, rosin acids and mixtures thereof, linked at an intermediary position along the fatty acid or rosin acid backbone by a direct bond, an ether linkage, or a peroxide linkage, and wherein each of the fatty acids and rosin acids is substituted by a maleic anhydride, fumaric acid, or (meth)acrylic acid.

An "oxidized and maleated composition" (hereinafter an "oxmal composition") is a composition comprising one or more oxmal compounds, wherein when the composition comprises more than one oxmal compound, the oxmal compounds can be the same or different. Non-limiting examples of oxmal compositions include tall oils, which have been maleated and oxidized; animal oils, which have been maleated and oxidized; plant oils, which have been maleated and oxidized; algal derived oils, which have been maleated and oxidized; and microbially derived oils, which have been maleated and oxidized. In some embodiments, oxmal compositions can also include one or more non-reacted or partially reacted species, such as non-maleated dimers, trimers, etc of fatty acids, rosin acids, and mixtures thereof.

The phrase "a compound, which has been maleated and oxidized" is used interchangeably with "a maleated and oxidized compound". The phrase "a composition, which has been maleated and oxidized" is used interchangeably with "a maleated and oxidized composition." The phrase "oxidized and maleated" is used interchangeably with "maleated and oxidized."

Wherever the phrase "for example", "such as", and the like are used herein, the phrase "and without limitation" is understood to follow unless explicitly stated otherwise. Therefore, "for example tall oil" means "for example and without limitation tall oil". Similarly all examples herein are non-limiting unless explicitly stated otherwise.

As used herein, the terms "maleated," "maleation," and the like refer to the modification of hydrocarbon-based backbone structures having one or more sites of unsaturation (e.g., $C_{1-8}$-fatty acids, such as linoleic acid and oleic acid), which introduces additional carboxylic moieties onto the molecules by reaction with one or more α,β unsaturated carboxylic acids or anhydrides. In some embodiments, an α,β unsaturated carboxylic acid or anhydride is chosen from maleic anhydride, fumaric acid, acrylic acid, and methacrylic acid (herein acrylic acid and methacrylic acid are generally referred to in the aggregate or alternative as (meth)acrylic acid). In some embodiments, an α,β unsaturated carboxylic acid or anhydride is a biogenically derived unsaturated carboxylic acid or anhydride.

As used herein, "acid functionality" in addition to its traditional meaning, also encompasses groups which are hydrolyzable such as anhydride groups.

As used herein, the terms "carboxylic moiety" and "carboxylic moieties" are also intended to include the anhydride structure formed by the condensation reaction between two carboxyl groups.

As used herein, "tall oil fatty acid" or "TOFA", consistent with industry standards, encompasses compositions which include not only fatty acids, but also rosin acids and/or unsaponifiables. TOFAs are generally produced as a distillation fraction of crude tall oil and therefore contain a mixture of saturated and unsaturated fatty acids, rosin acids, and mixtures thereof.

As used herein, "alkyl," "alkenyl" and "alkynyl" carbon chains, if not specified, should be broadly interpreted, for example to encompass substituted or unsubstituted, straight, branched, and cyclic "chains."

As used herein, "polyolefin oligomers" in addition to its traditional meaning, also encompasses oligomers having one site of unsaturation.

As used herein, "about" is meant to account for variations due to experimental error.

II. Compounds

Oxmal compounds provided herein comprise at least two or more hydrocarbon-based backbone structures, wherein at least one backbone structure is substituted by at least one α,β unsaturated carboxylic acid or anhydride, and further wherein each backbone structure is linked to one other backbone structure by a bridging group chosen from a direct bond, an ether linkage, or a peroxide linkage located at a non-terminal position of each backbone structure.

The hydrocarbon backbone structure can be chosen from, for example, substituted and unsubstituted straight-chain, branched-chain and polycyclic hydrocarbons. The hydrocarbon backbone structure can be chosen, for example, from fatty acids and rosin acids. The hydrocarbon backbone structure can be chosen from, for example, $C_{10}$-$C_{22}$ fatty acids. The hydrocarbon backbone structure can be chosen from, for example, $C_{16}$-$C_{22}$ fatty acids. The hydrocarbon backbone structure can be chosen from, for example, $C_{16}$-$C_{18}$ fatty acids. The hydrocarbon backbone structure can be, for example, a $C_{18}$ fatty acid. The hydrocarbon backbone structure can be chosen from, for example, oleic, linoleic, and linolenic acid.

In some embodiments, the hydrocarbon-backbone structure is chosen from polyolefin oligomers having at least one reactive allylic site. In some embodiments, polyolefin oligomers have at least one site of unsaturation. In some embodiments, polyolefin oligomers have at least two sites of unsaturation. In some embodiments, polyolefin oligomers have at least three sites of unsaturation. In some embodiments, the polyolefin oligomers have from 10 to 24 carbons and at least one site of unsaturation. In some embodiments, polyolefin oligomers have from 10 to 24 carbons and from one to five sites of unsaturation. In some embodiments, polyolefin oligomers have from 10 to 24 carbons and from one to three sites of unsaturation. In some embodiments, the polyolefin oligomers have from 16-18 carbons and from one to three sites of unsaturation. In some embodiments, the polyolefin oligomers have 16 or 18 carbons and two sites of unsaturation. In some embodiments, the hydrocarbon-backbone structure could be chosen from non-natural fatty acids, for example fatty acids having odd chain lengths, or 14 carbon chain lengths. In some embodiments, the hydrocarbon-backbone structures chosen from non-natural fatty acids comprise from 1 to 3 sites of unsaturation, for example 2, or for example 3 sites of unsaturation.

In some embodiments, the α,β unsaturated carboxylic acid or anhydride can be a biogenically derived α,β unsaturated carboxylic acid or anhydride. Non-limiting examples of biogenically derived α,β unsaturated carboxylic acids or anhydrides include itaconic acid, itaconic anhydride, aconitic acid, aconitic anhydride, acrylic acid, methacrylic acid, citraconic acid, citraconic anhydride, mesaconic acid, muconic acid, glutaconic acid, methylglutaconic acid, traumatic acid, and fumaric acid. The acids and anhydrides include any isomers (e.g., enantiomers, diastereomers, and cis-/trans-isomers), and salts. In some embodiments, the α,β unsaturated carboxylic acid or anhydride can be maleic anhydride, fumaric acid, or (meth)acrylic acid.

In certain embodiments all of the hydrocarbon-based backbone structures of an oxmal compound are maleated. In other embodiments, only some, for example, only one of the hydrocarbon-based backbone structures of an oxmal compound are maleated. In some embodiments, two of the hydrocarbon-based backbone structures of an oxmal compound are maleated. In some embodiments, at least one of the hydrocarbon-based backbone structures of an oxmal compound is maleated.

Oxmal compounds within the scope of the invention include oxidized and maleated unsaturated fatty acid compounds of formula I:

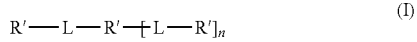

(I)

wherein L is chosen from a direct bond, —O—, or —OO—; n is a number chosen from 0, 1, 2, 3, 4, and 5; and R' is a compound of formula II:

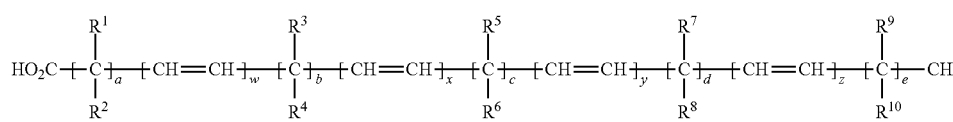

(II)

wherein a, b, c, d, and e are independently a number from 0 to 20; w, x, y, and z are independently 0 or 1; $R^1$-$R^{10}$ are each independently chosen from L, H, alkyl, alkenyl, alkynyl, alkoxy, amino, hydroxy, and X; wherein at least one of $R^1$-$R^{10}$ is X; and wherein at least one of $R^1$-$R^{10}$ is L; wherein X is an α,β unsaturated carboxylic acid or anhydride; wherein the sum of a, b, c, d, e, w, x, y, and z is a number from 8 to 22; and wherein at least one of w, x, y, and z is 1. In some embodiments, the sum of a, b, c, d, e, w, x, y, and z is a number from 12 to 18, while in other embodiments, the sum of a, b, c, d, e, w, x, y, and z is 16. In some embodiments, X is chosen from maleic anhydride, fumaric acid, and (meth)acrylic acid. In some embodiments, X is chosen from

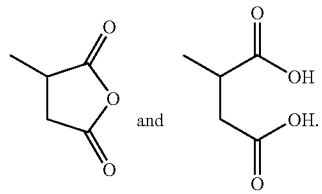

In some embodiments, n is 0 or 1. In some embodiments each R' does not require a substitution with X to be present as long as at least one of R' in the compound of Formula I does contain at least one X.

In some embodiments, the oxmal compounds have two or three hydrocarbon-based backbone structures (for example, two or three R' structures of formula II), and each of the hydrocarbon-based backbone structures is of the same type. For example, without limitation, each of the two or three hydrocarbon-based backbone structures can be a fatty acid. In some embodiments, the oxmal compounds comprise two or three hydrocarbon-based backbone structures, wherein each of the hydrocarbon-based backbone structures is the same. Formulas 3-5, 9-11, 15-17, 24, and 25 below are examples of oxmal compounds having backbone structures chosen from the same fatty acid. Non-limiting examples of oxidized and maleated fatty acids having two hydrocarbon-based backbone structures that are the same include: oxidized and maleated decenoic acid; oxidized and maleated dodecenoic acid; oxidized and maleated cis-9-tetradecenoic acid; oxidized and maleated cis-9-hexadecenoic acid; oxidized and maleated oleic acid; oxidized and maleated linoleic acid; oxidized and maleated linolenic acid; oxidized and maleated cis-6,cis-9,cis-12,cis-15-octadecatetraenoic acid; oxidized and maleated ricinoleic acid; oxidized and maleated cis-9-eicosenoic acid; oxidized and maleated cis-11-eicosenoic acid; oxidized and maleated eicosadienoic acid; oxidized and maleated eicosatrienoic acid; oxidized and maleated arachidonic acid; oxidized and maleated eicosapentaenoic acid; oxidized and maleated erucic acid; oxidized and maleated docosadienoic acid; oxidized and maleated 4,8,12,15,19-docosapentaenoic acid; oxidized and maleated docosahexaenoic acid; and oxidized and maleated tetracosenoic acid.

In some embodiments, the oxmal compounds have two different hydrocarbon-based backbone structures. For example, without limitation, one of the hydrocarbon-based structures can be chosen from fatty acids and one can be chosen from rosin acids. Formulas 6-8, 12-14, and 18-20 below are examples of oxmal compounds having one rosin acid hydrocarbon-based backbone structure and one fatty acid hydrocarbon-based backbone structure. As another non-limiting example, the hydrocarbon backbone-structures can be two different fatty acids. For example, without limitation, one of the hydrocarbon-based backbone structures can be oleic acid and one of the hydrocarbon-based backbone structures can be linoleic acid.

Non-limiting specific structure examples of oxmal compounds in accordance with the invention are illustrated as Formulas 3-27 below. These examples illustrate one of the expected isomeric forms, it is to be expected that other isomers (e.g., cis and trans isomers) can be prepared and accordingly are within the scope of the invention.
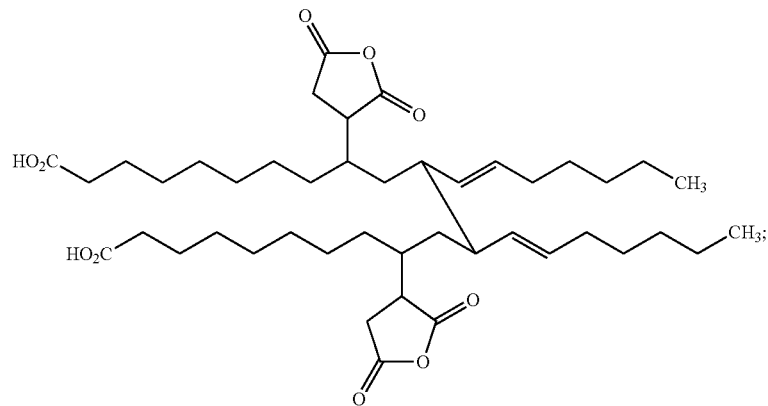
(III)
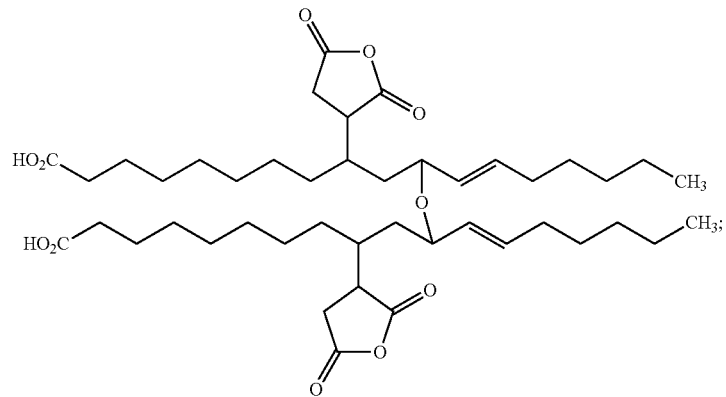
(IV)
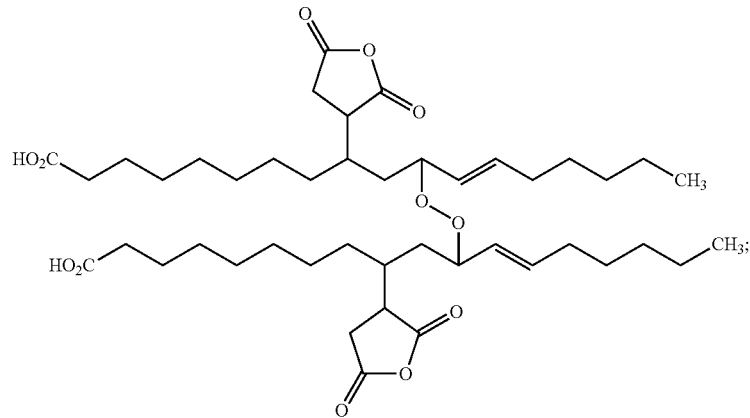
(V)

-continued
(VI)
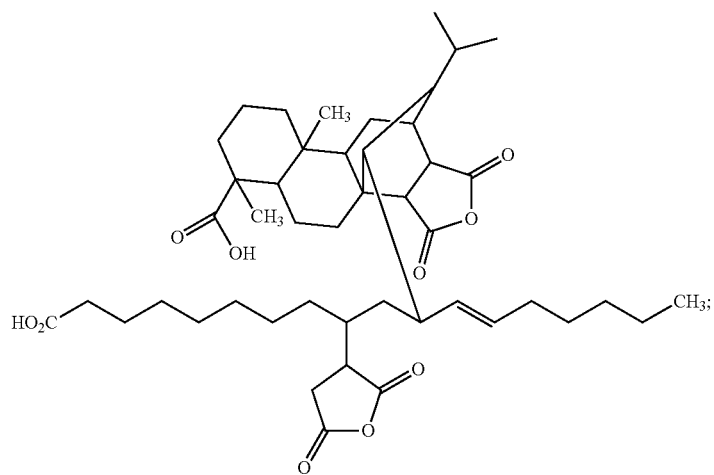
(VII)
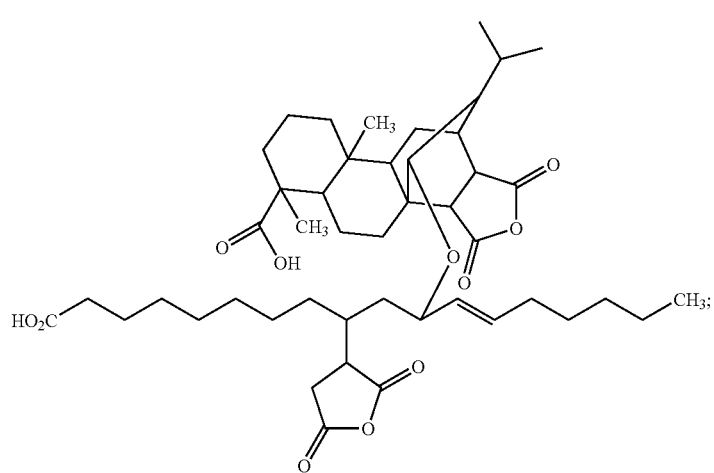
(VIII)
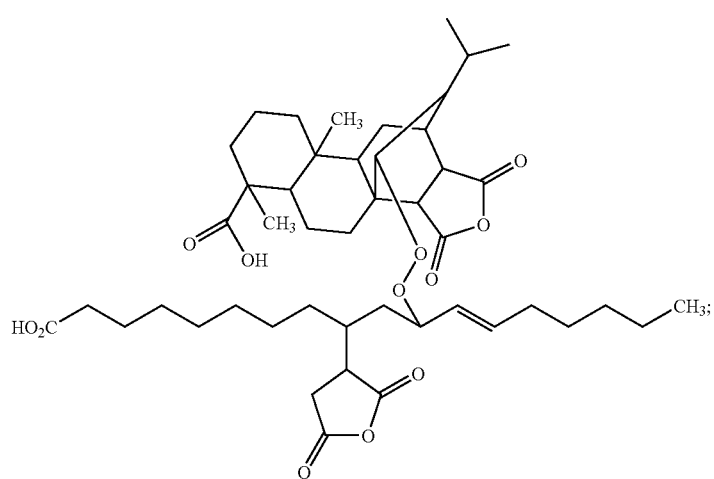

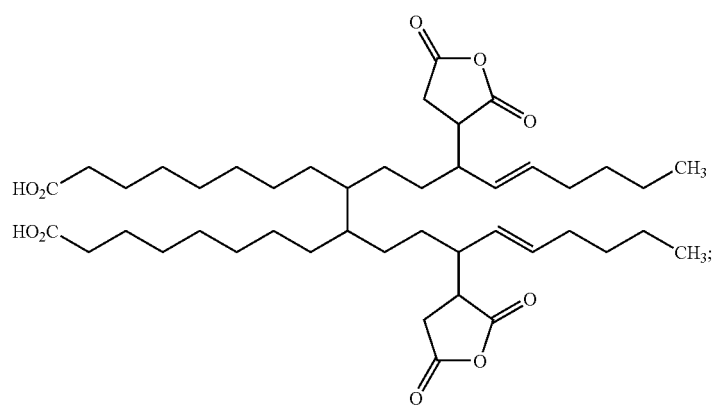
(IX)
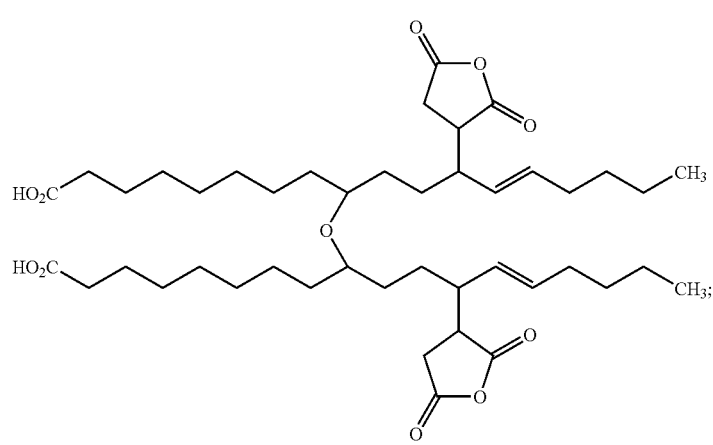
(X)
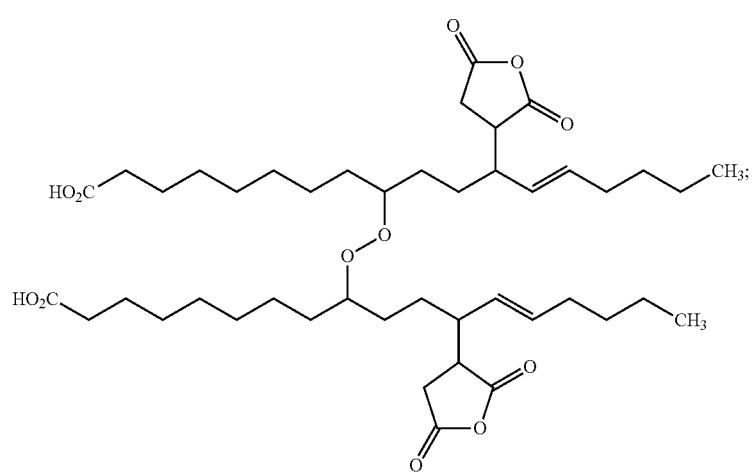
(XI)

(XII)
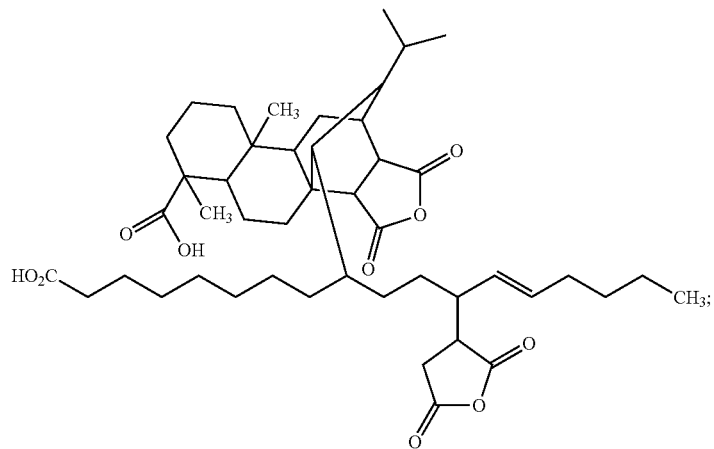
(XIII)
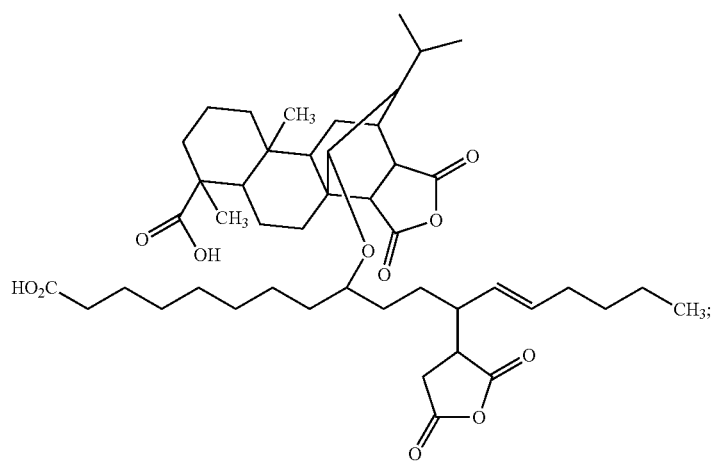
(XIV)
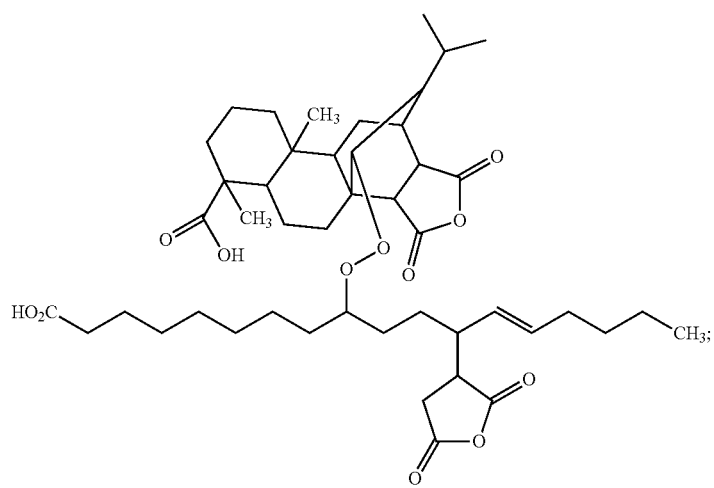

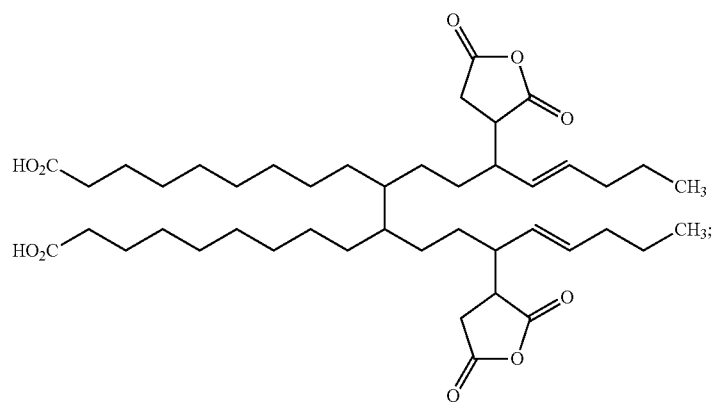
(XV)
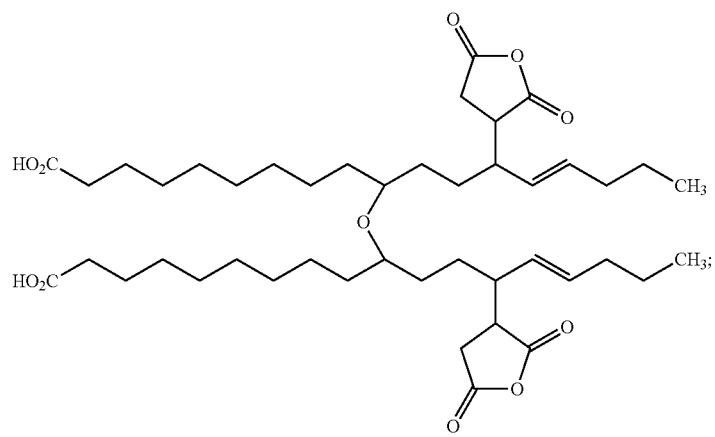
(XVI)
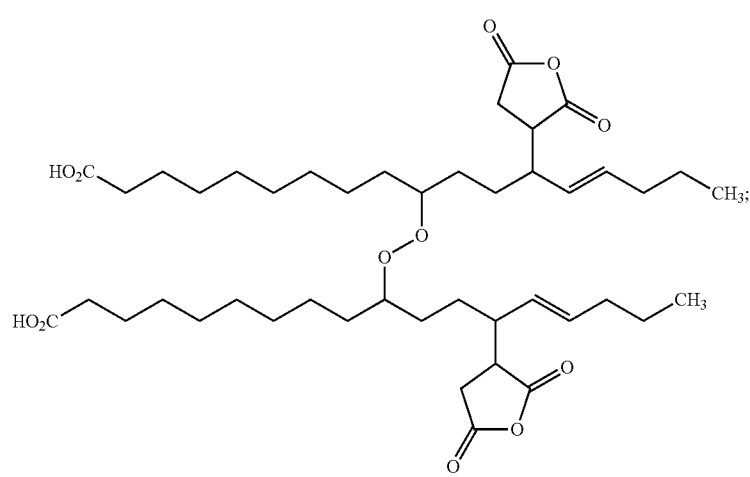
(XVII)

-continued
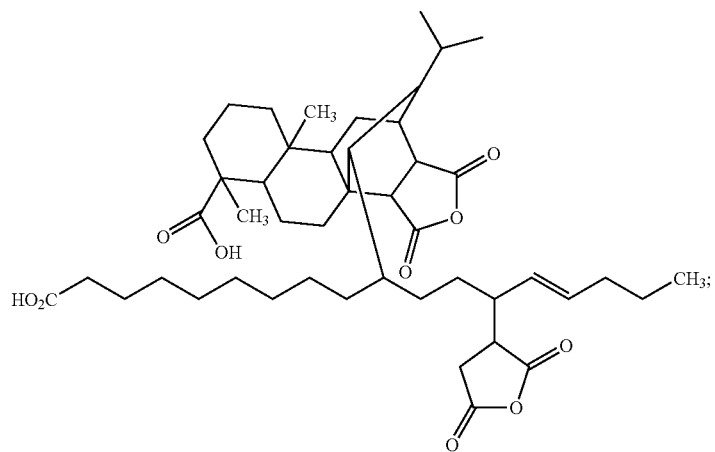
(XVIII)
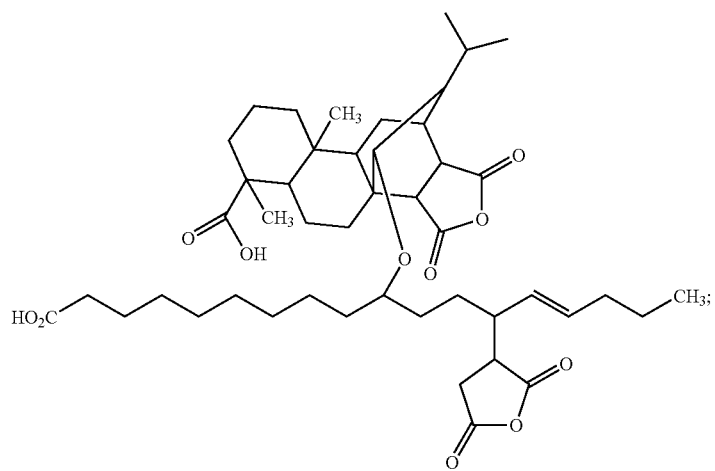
(XIX)
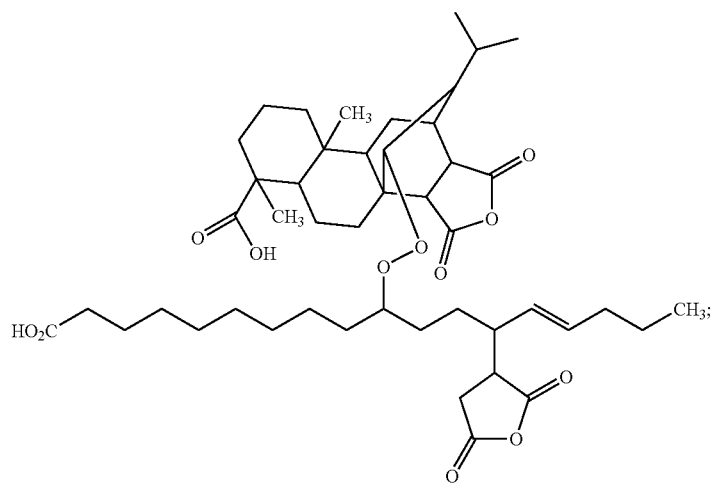
(XX)

(XXI)
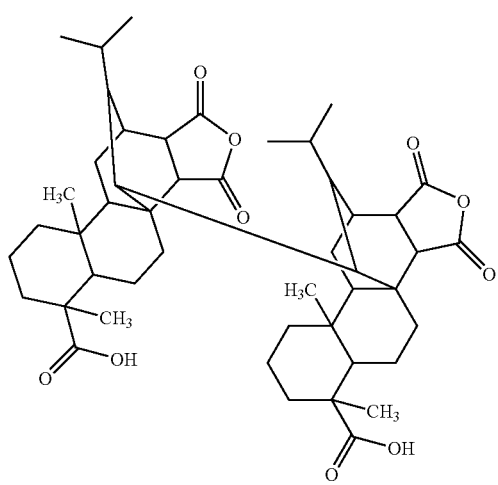
(XXII)
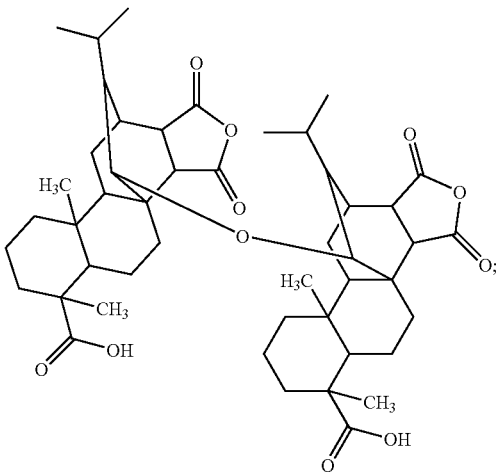
(XXIII)
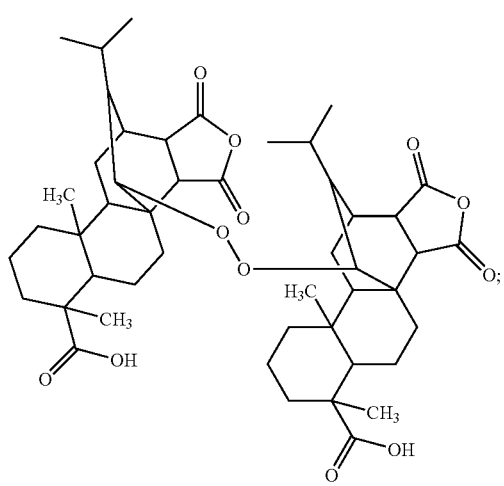
(XXIV)
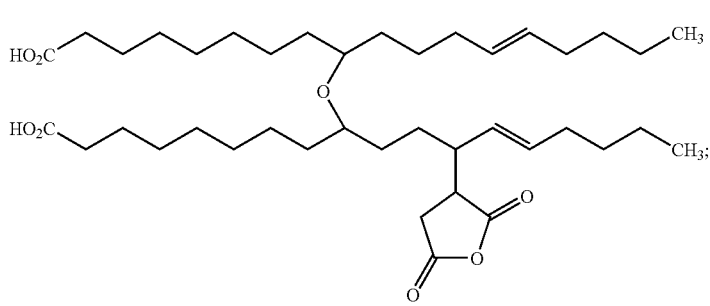
(XXV)
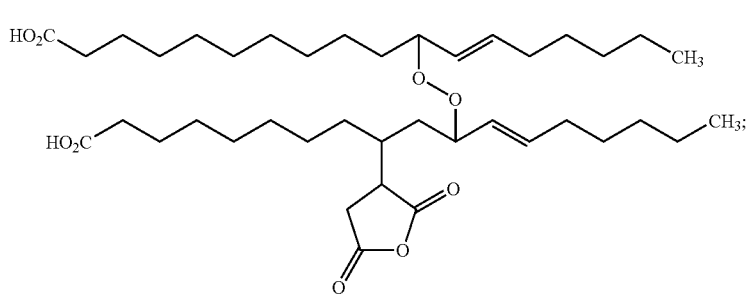

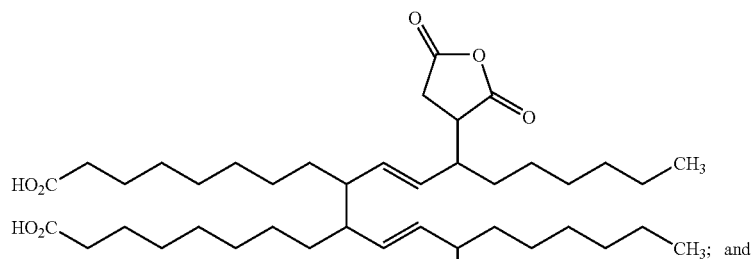

(XXVI)

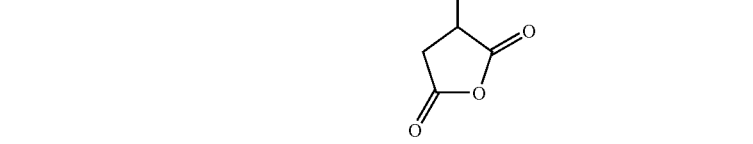

(XXVII)

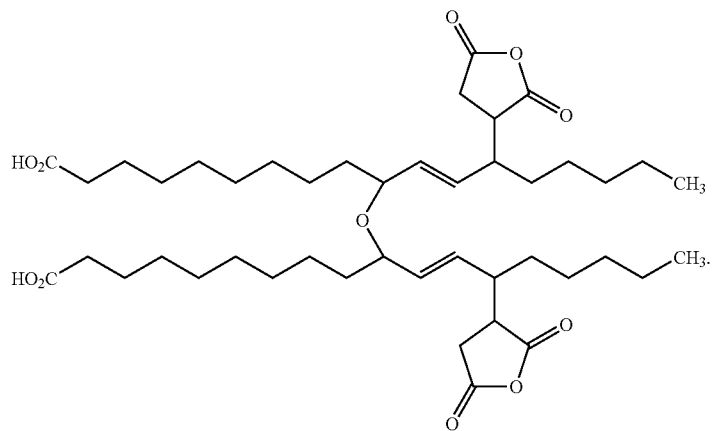

II. Compositions

Oxmal compositions provided herein comprise one or more oxmal compounds, wherein when the composition comprises more than one oxmal compound, the oxmal compounds can be the same or different. Non-limiting examples of oxmal compositions, are compositions comprising one or more of the oxmal compounds disclosed above, such as compositions containing one or more of oxidized and maleated decenoic acid; oxidized and maleated dodecenoic acid; oxidized and maleated cis-9-tetradecenoic acid; oxidized and maleated cis-9-hexadecenoic acid; oxidized and maleated oleic acid; oxidized and maleated linoleic acid; oxidized and maleated linolenic acid; oxidized and maleated cis-6,cis-9, cis-12,cis-15-octadecatetraenoic acid; oxidized and maleated ricinoleic acid; oxidized and maleated cis-9-eicosenoic acid; oxidized and maleated cis-11-eicosenoic acid; oxidized and maleated eicosadienoic acid; oxidized and maleated eicosatrienoic acid; oxidized and maleated arachidonic acid; oxidized and maleated eicosapentaenoic acid; oxidized and maleated erucic acid; oxidized and maleated docosadienoic acid; oxidized and maleated 4,8,12,15,19-docosapentaenoic acid; oxidized and maleated docosahexaenoic acid; and oxidized and maleated tetracosenoic acid. In some embodiments, an oxmal composition comprises one or more of oxidized and maleated oleic acid; oxidized and maleated linoleic acid; oxidized and maleated linolenic acid; oxidized and maleated cis-9-eicosenoic acid; and oxidized and maleated cis-11-eicosenoic acid. In another embodiment, the composition has one or more of oxidized and maleated oleic acid; oxidized and maleated linoleic acid; and oxidized and maleated linolenic acid. In a further embodiment, the composition includes oxidized and maleated oleic acid. In a further embodiment, the composition includes one or more compounds of Formula 3-27.

In some embodiments, the oxmal compositions are a source of fatty acids, rosin acids, and mixtures of fatty acids and rosin acids that have been oxidized and/or maleated. Sources of fatty acids, rosin acids, and mixtures thereof, can be, for example, any natural or synthetic oil, including algal produced and microbial produced oil, that includes at least one site of unsaturation. In certain cases, the distillation products or distillation residues of such oils can serve as the source of fatty acids, rosin acids, and mixtures thereof (e.g. distilled tall oil and tall oil distillation bottoms). In some embodiments, the natural or synthetic oil includes one site of unsaturation, two sites of unsaturation, or more. In some embodiments, the natural or synthetic oil includes at least one site of unsaturation. In some embodiments, the natural or synthetic oil comprises from 10 to 24 carbons and at least one site of unsaturation. In some embodiments, the natural or synthetic oil comprises from 16 to 22 carbons and from one to five sites of unsaturation. In some embodiments, the natural or synthetic oil comprises from 16 to 22 carbons and from one to three sites of unsaturation. In some embodiments, the natural or synthetic oil comprises 18 carbons and two sites of unsaturation. In other embodiments, these oils can contain a fatty acid having 14 carbons and three sites of unsaturation. In some embodiments, these oils can contain as one significant constituent, linoleic acid, an unsaturated long chain fatty acid, and may also contain other unsaturated fatty acids and rosin acids. In another embodiment, these oils can contain as one significant constituent, oleic acid.

Natural sources of fatty acids, rosin acids, and mixtures thereof, include plant- or animal-based oil compositions. For example, plant- and animal-based oils having double bonds, i.e., sites of unsaturation in their hydrocarbon chains can be oxidized and maleated to produce oxmal compositions according to the invention. Depending on the level of maleation, the compositions may also include unreacted or partially reacted species such as free fatty acid and rosin acid, maleated but not oxidized fatty acid and rosin acid, oxidized but not maleated fatty acid and rosin acid, and oxidized and partially maleated fatty acid and rosin acid. Non-limiting examples of plant- and animal-based oils include: canola oil; castor oil; coco butter; coconut oil; corn oil; cotton seed oil; crambe oil; linseed oil; olive oil; palm kernel oil; palm oil; peanut oil; rape seed oil; safflower oil; soybean oil; sunflower seed oil; tall oil; tung oil; butter; lard; tallow; yellow grease; and fish oil (e.g., herring oil, menhaden oil, and sardine oil). Oils can be oxidized and/or maleated directly, or if present in a combined form such as triglycerides, can be saponified to their component fatty acids before the oxidation and/or maleation reactions.

In certain embodiments, the source of fatty acids, rosin acids, and/or mixtures thereof is a plant- or animal-based oil chosen from fish oil, corn oil, soybean oil, and tall oil.

In certain embodiments, the source of fatty acids, rosin acids, and/or mixtures thereof is a plant- or animal-based oil chosen from tall oils and tall oil products. In some embodiments, tall oil products are maleated tall oil products. In some embodiments, the tall oil products are oxidized tall oil products. More generally, non-limiting examples of tall oil sources of fatty acids, rosin acids, and mixtures thereof include various tall oil products such as without limitation a tall oil itself, crude tall oil, distilled tall oil products, tall oil fatty acid (TOFA), TOFA which has been maleated in a range of from about 6% to about 25%, rosin acids, tall oil distillation bottoms, and specialty tall oil products such as those provided by Georgia-Pacific Chemicals LLC, Atlanta, Ga. For example, tall oil distillation products having greater than about 90% tall oil fatty acid and less than about 6% rosin acid, such as XTOL® 100, XTOL® 1101, XTOL® 300, and XTOL® 304; tall oil distillation products such as XTOL® 520, XTOL® 530 and XTOL® 542; tall oil distillation products having at least about 90% rosin acid and less than about 5% tall oil fatty acid, such as LYTOR® 100 and LYTOR® 101; tall oil blends of tall oil fatty acid distillation bottoms and a distilled tall oil, which blend has been maleated, such as XTOL® 690, XTOL® 692; oxidized crude tall oil compositions, such as XTOL® MTO; and blends thereof.

Sources of fatty acids, rosin acids, and mixtures thereof can include various amounts of the fatty acids, rosin acids, and mixtures thereof, including various amounts of different fatty acids and rosin acids. For example, TOFA can contain oleic acid, linoleic acid, and linolenic acid, as well as rosin acids, such as abietic and pimaric acid. In some cases, the compositions may further include unsaponifiables or neutral compounds, such as hydrocarbons, higher alcohols, and sterols.

In certain embodiments, a blend of tall oil fatty acid and rosin acid can be used as the source of fatty acids and rosin acids (i.e. the source of hydrocarbon-based backbone structures) to be oxidized and maleated. Such a blend can contain, for example, from about 20% to 99% tall oil fatty acid (e.g., 20%, 25%, 30%, 45%, 50%, 60%, 75%, 82%, 90%, and 99%) and about 1% to about 55% rosin acid (e.g., 1%, 2.5%, 5%, 10%, 15%, 20%, 25%, 30%, 40%, 50%, and 55%). In some embodiments a blend can contain about 45% to about 90% tall oil fatty acid. In some embodiments a blend can contain about 30% tall oil fatty acid and about 30% rosin acid. In another embodiment, the ratio of tall oil fatty acid to rosin acid can be from about 3:2 to about 4:1 (e.g., 3:2, 4:2, 3:1, and 4:1).

As one non-limiting example, the oxmal composition can be a crude tall oil composition that has been oxidized and maleated (see Example 3). As another non-limiting example, the oxmal composition can be a tall oil fatty acid (TOFA) composition that has been oxidized and maleated (see Example 4).

In some embodiments, the oxmal compositions are a source of maleated tall oil product that has been oxidized. As one non-limiting example, the oxmal composition is a XTOL® 690 that has been oxidized (see Example 1). As another non-limiting example, the oxmal composition is a XTOL® 692 that has been oxidized (see Example 1).

In some embodiments, the oxmal composition is a source of oxidized tall oil product that has been maleated. As one non-limiting example, the oxmal composition is a XTOL® MTO that has been maleated (see Example 2).

Figure 2:
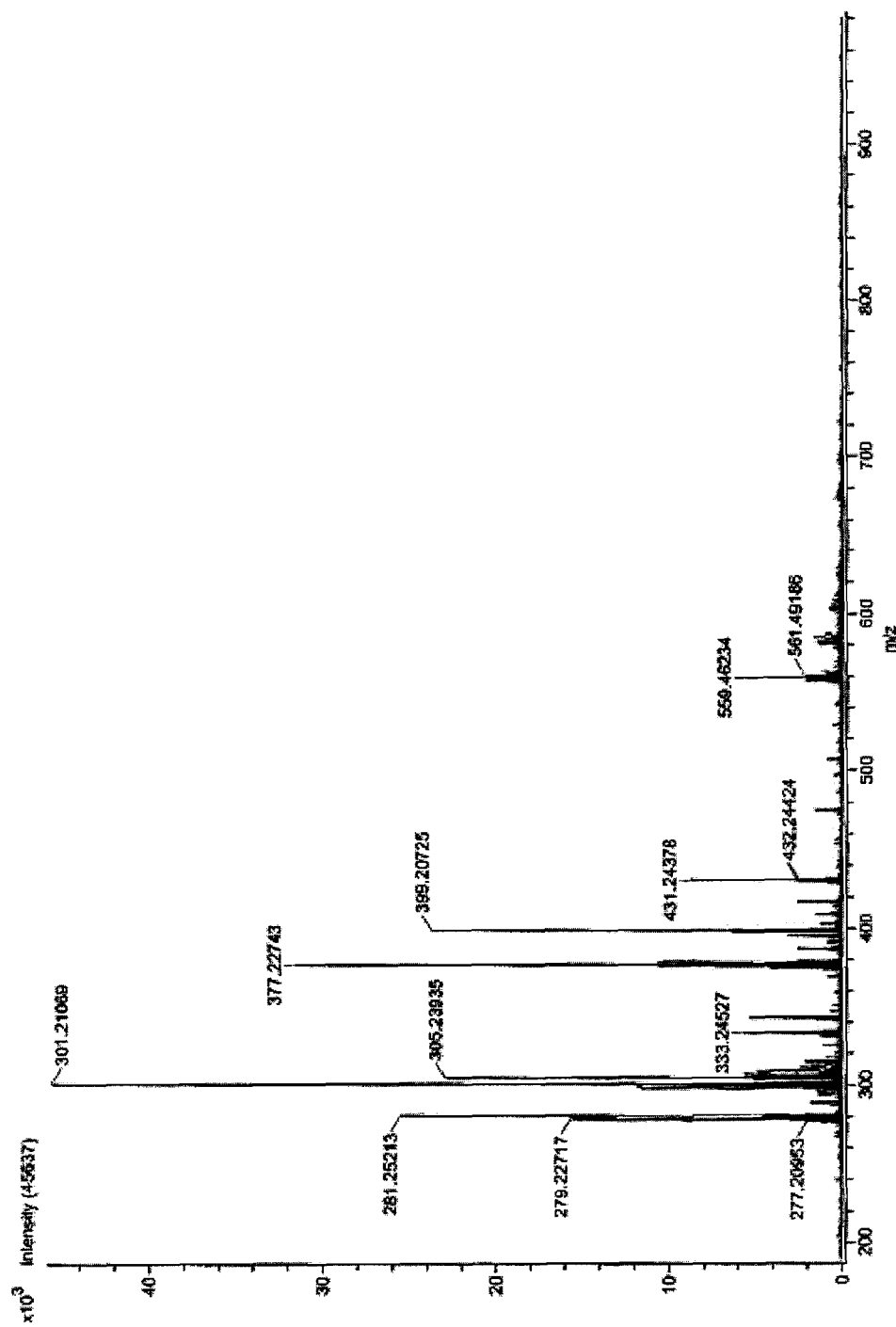
FIG. 2 is a time-of-flight mass spectrum of an oxidized XTOL® 690.
Figure 3:
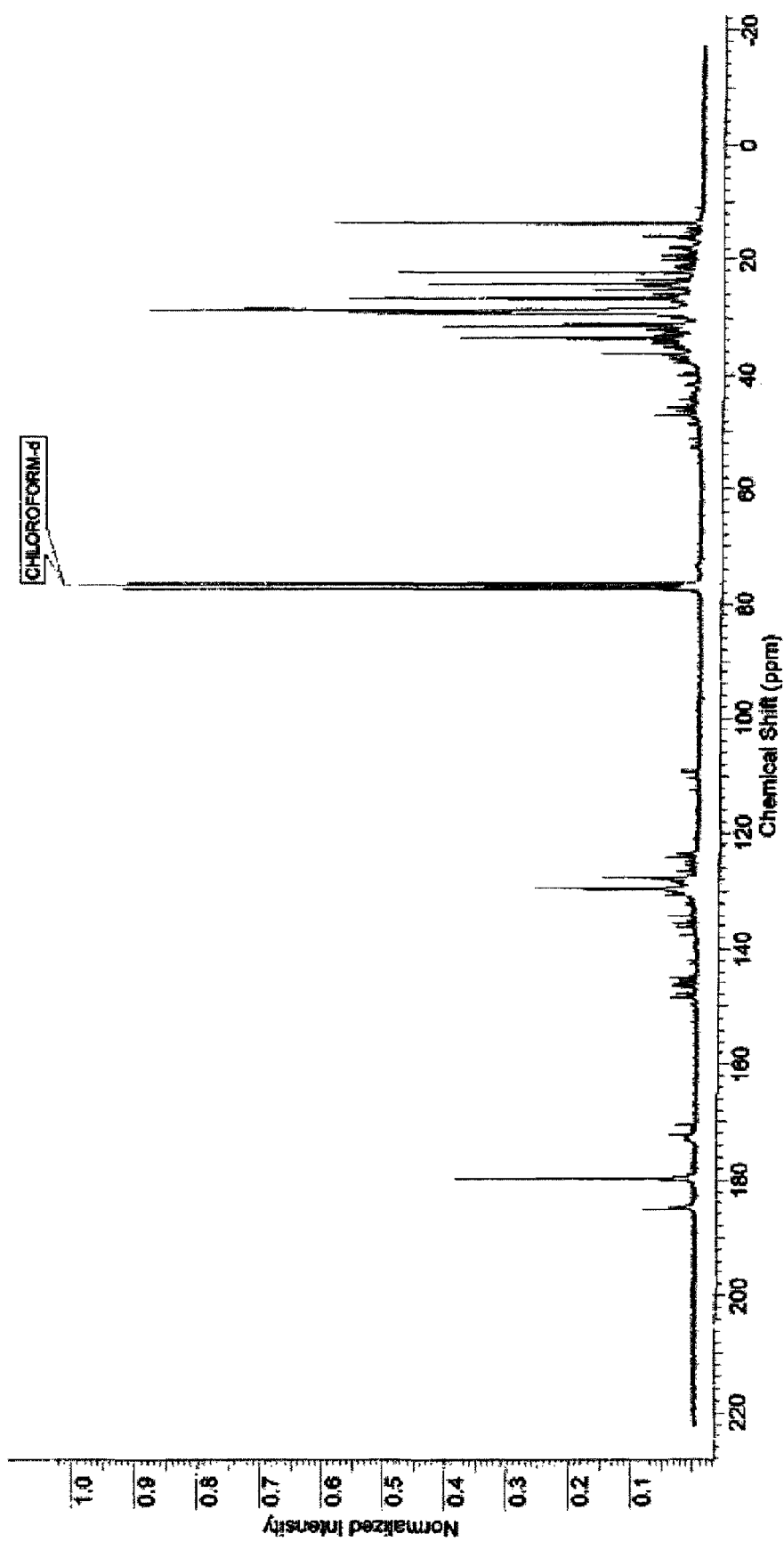
FIG. 3 is a $^{13}$C NMR spectrum of an oxidized XTOL® 690.
Figure 4:
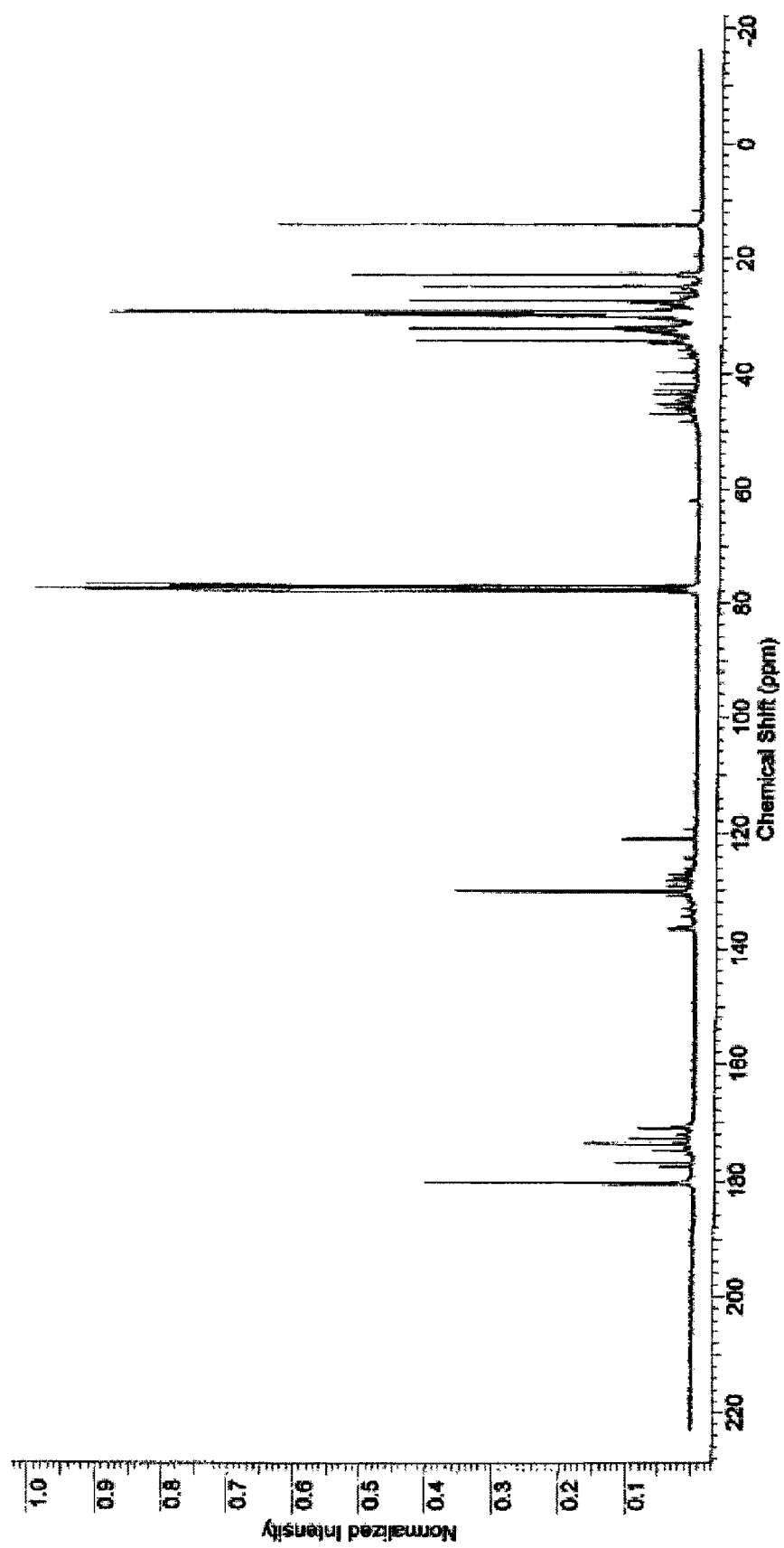
FIG. 4 is a $^{13}$C NMR spectrum of an oxidized and maleated TOFA.
Figure 5:
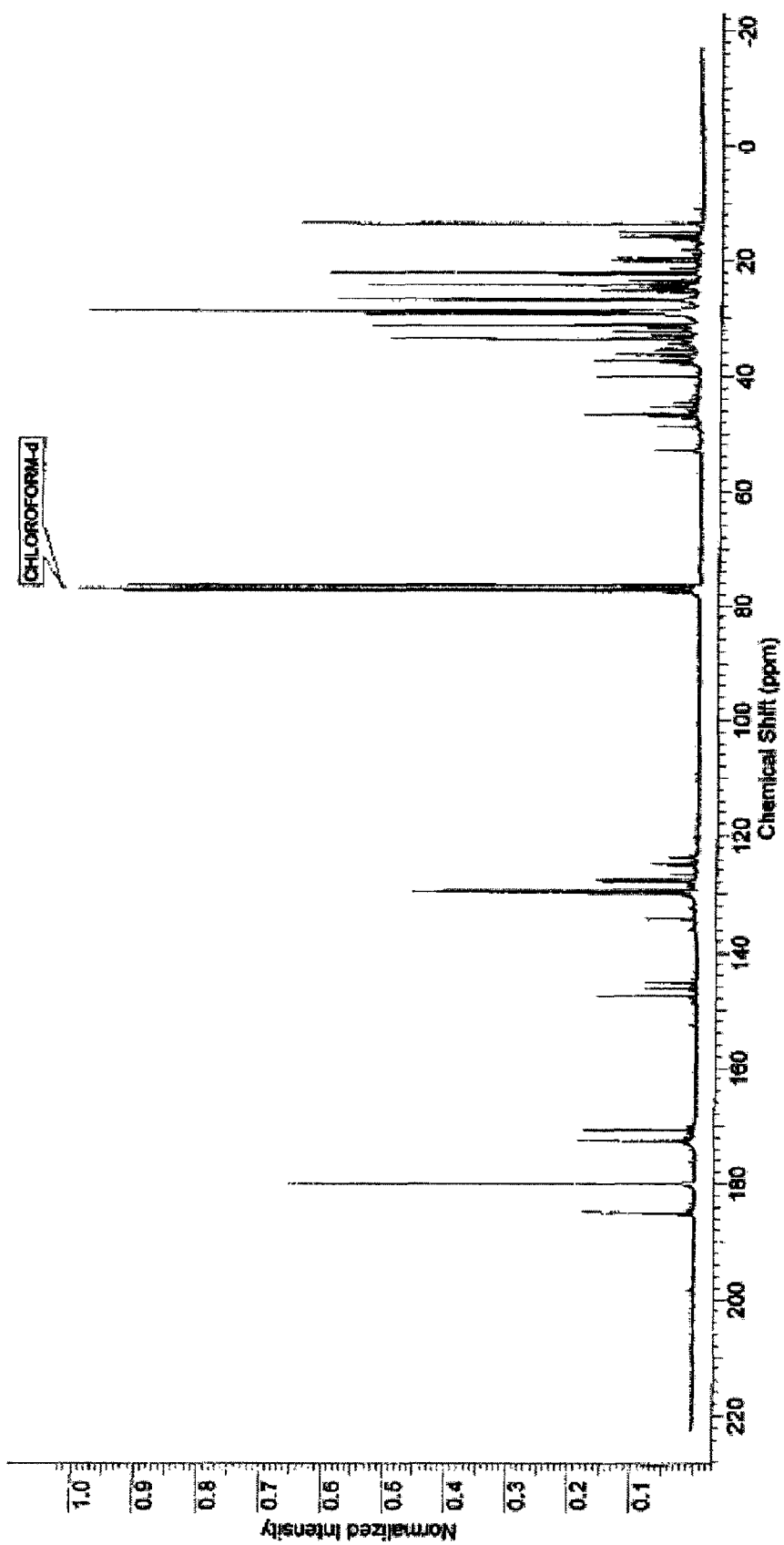
FIG. 5 is a $^{13}$C NMR spectrum of an oxidized XTOL® 692.
Figure 6:
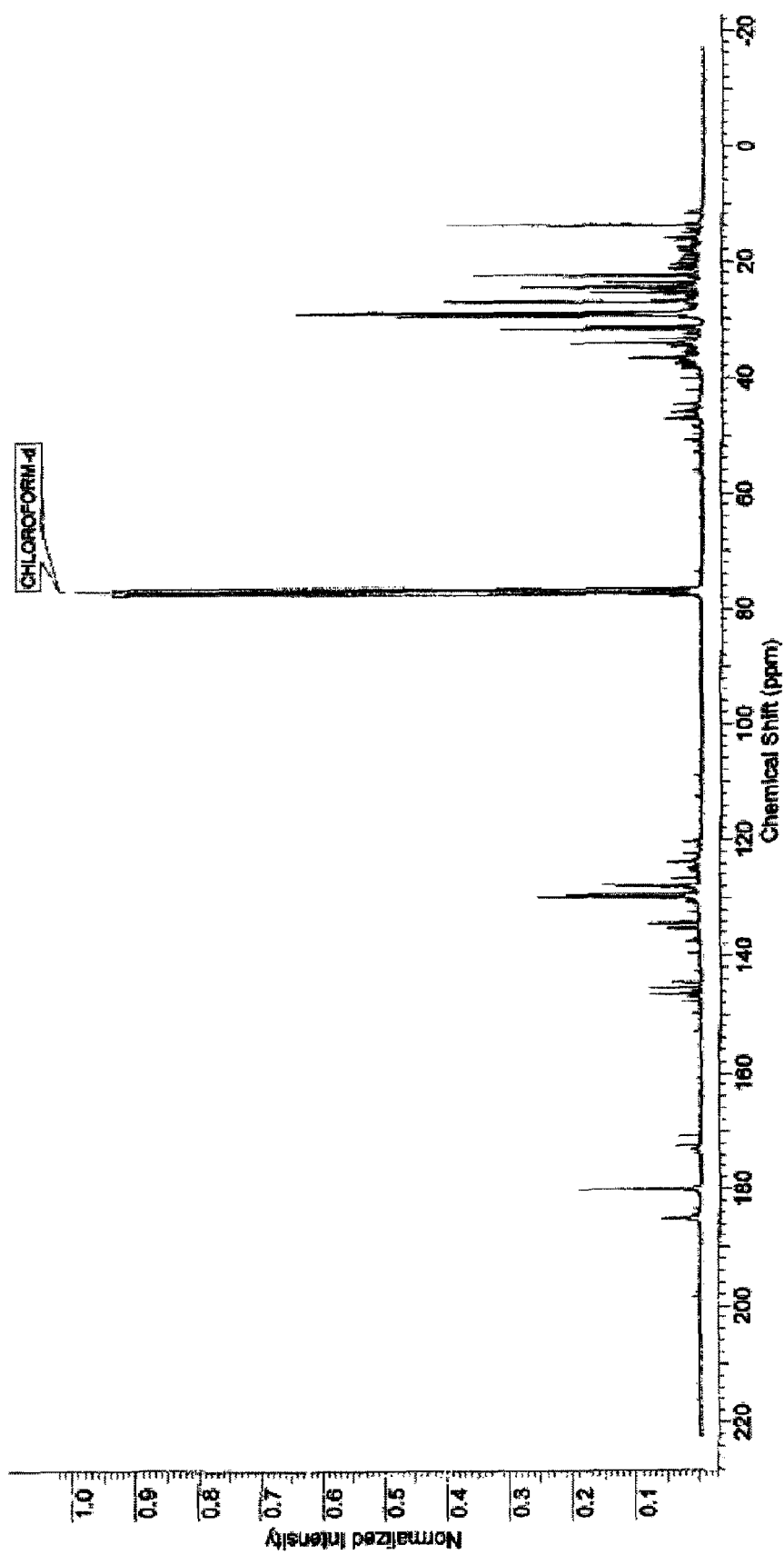
FIG. 6 is a $^{13}C$ NMR spectrum of a maleated XTOL® MTO.

Referring now to the figures, FIG. 1 shows, in a non-limiting example, a time-of-flight mass spectrum (TOF MS) of an oxidized and maleated TOFA composition. This is a typical TOF MS obtained from the oxmal compositions of Example 4. FIG. 2 shows, in a non-limiting example, a TOF MS of an oxidized XTOL® 690. This is a typical TOF MS obtained from the oxmal compositions of Example 1. FIG. 3 shows, in a non-limiting example, a $^{13}$C-NMR spectrum of an oxidized XTOL® 690. This is a typical $^{13}$C-NMR spectrum obtained from the oxmal compositions of Example 1. FIG. 4 shows, in a non-limiting example, a $^{13}$C-NMR spectrum of an oxidized and maleated TOFA composition. This is a typical $^{13}$C-NMR spectrum obtained from the oxmal compositions of Example 4. FIG. 5 shows, in a non-limiting example, a $^{13}$C-NMR spectrum of an oxidized XTOL® 692. This is a typical $^{13}$C-NMR spectrum obtained from the oxmal compositions of Example 1. FIG. 6 shows, in a non-limiting example, a $^{13}$C-NMR spectrum of a maleated XTOL® MTO. This is a typical $^{13}$C-NMR spectrum obtained from the oxmal compositions of Example 2. Based on the spectral data and tall oil chemistry, it is believed that the compositions produced in Examples 1, 2, and 4 include one or more of the compounds shown in Formulas 3-27.

In another embodiment, an oxmal composition can include an acid compound having at least a first backbone and a second backbone linked by a linking group. The linking group can be a direct bond, an ether linkage, or a peroxide linkage. In some embodiments, the first and second backbone can be independently chosen from a maleated unsaturated fatty acid or maleated rosin acid. In some embodiments, the first backbone is chosen from a maleated unsaturated fatty acid or maleated rosin acid and the second backbone is chosen from an unsaturated fatty acid or rosin acid.

Non-limiting examples of maleated unsaturated fatty acids can include: maleated decenoic acid; maleated dodecenoic acid; maleated cis-9-tetradecenoic acid; maleated cis-9-hexadecenoic acid; maleated oleic acid; maleated linoleic acid; maleated linolenic acid; maleated cis-6,cis-9,cis-12,cis-15-octadecatetraenoic acid; maleated ricinoleic acid; maleated cis-9-eicosenoic acid; maleated cis-11-eicosenoic acid; maleated eicosadienoic acid; maleated eicosatrienoic acid; maleated arachidonic acid; maleated eicosapentaenoic acid; maleated erucic acid; maleated docosadienoic acid; maleated 4,8,12,15,19-docosapentaenoic acid; maleated docosahexaenoic acid; and maleated tetracosenoic acid.

In certain embodiments, the maleated unsaturated fatty acid is maleated oleic acid; maleated linoleic acid; maleated linolenic acid; maleated cis-9-eicosenoic acid; or maleated cis-11-eicosenoic acid. In another embodiment, the maleated unsaturated fatty acid is maleated oleic acid; maleated linoleic acid; and maleated linolenic acid. In a further embodiment, the maleated unsaturated fatty acid is maleated oleic acid.

In certain embodiments, an oxmal composition can include compounds having at least three acid functionalities (e.g., three, four, five, six, seven, eight, nine, ten, eleven, or twelve acid functionalities). In some embodiments, an oxmal composition can include compounds having at least six acid functionalities.

In certain embodiments, the oxmal composition can be maleated from about 2% to about 40% by weight (e.g., 2%, 3.5%, 5%, 6%, 7.5%, 8%, 10%, 12%, and 15%). In some embodiments, the percent maleation is from about 2% to about 25% by weight. In one embodiment, the percent maleation is 3.5% by weight, while in another embodiment, the percent maleation is 12% by weight. In some embodiments, the percent maleation is 5% by weight. In some embodiments, the percent maleation is 6% by weight. The composition of products prepared is related to the percent maleation performed. Accordingly, in some oxmal compositions, oxmal compounds may include compounds that have been maleated, for example, on at least one hydrocarbon-based backbone structure, at least two hydrocarbon-based backbone structures, on all hydrocarbon-based backbone structures. In certain embodiments, an oxmal composition may further comprise compounds that have been oxidized but have not been maleated.

An oxmal composition can be characterized by its acid value. As used herein, an "acid value" is the mass of potassium hydroxide (KOH) in milligrams that is required to neutralize one gram of an oxmal composition. The acid value can be used as a measure of the amount of carboxylic acid groups in an oxmal composition. In a typical procedure, a known amount of an oxmal composition is dissolved in organic solvent and is titrated with a solution of potassium hydroxide of known concentration. The acid value can be determined by using a potassium hydride solution that contains phenolphthalein as a color indicator or using potentiometric analysis. Standard methods used for determining acid value are ASTM D 465-05 and AOCS Te 1a-64.

In some embodiments, the acid value can be from about 50 mg KOH/g to about 400 mg KOH/g (e.g., 65 mg KOH/g; 100 mg KOH/g; 150 mg KOH/g, 200 mg KOH/g; 330 mg KOH/g; and 400 mg KOH/g). In some embodiments, the acid value can be from about 150 mg KOH/g to about 300 mg KOH/g. In some embodiments, the acid value can be from about 150 mg KOH/g to about 225 mg KOH/g. In certain embodiments, the acid value can range from about 200 mg KOH/g to about 300 mg KOH/g. In other embodiments, the acid value is about 200 mg KOH/g.

Viscosity of an oxmal composition is another method of characterizing these compositions. Without being bound by theory, the viscosity of an oxmal composition increases, compared to the viscosity of the starting composition, with an increase in acid functionality. Both a Gardner-Holdt and a Brookfield Viscosity value can be used to characterize an oxmal composition. An apparent viscosity can be determined using a Brookfield viscometer. This measures the torque required to rotate a spindle at constant speed in a solution of an oxmal composition at 25° C. Standard test methods used for measuring Brookfield viscosity are ASTM D 803-03 and AOCS Ja 10-87 (93). In certain embodiments, the viscosity range for the oxmal products can range from about 1000 to 27,000 cPs @ 25° C. Standard test methods for determining Gardner-Holdt viscosity are ASTM D1545-07 and AOCS Ja 11-87 (93).

III. Preparation of Oxidized and Maleated Unsaturated Fatty Acid Compositions

Processes for preparing oxmal compounds and compositions, as described above, are also provided herein. Although the examples and descriptions herein emphasize methods of making compositions, the chemistry is equally applicable to methods of making compounds.

In some embodiments, an oxmal compound is prepared by oxidizing and maleating a hydrocarbon-based backbone structure having at least one site of unsaturation and at least one reactive allylic site. The hydrocarbon-backbone based structure can be, for example, a fatty acid, a rosin acid, or a polyolefin oligomer with at least one reactive allylic site. In some embodiments, the hydrocarbon-backbone structure is a $C_{16}$ or $C_{18}$ fatty acid, such as for example oleic acid, linoleic acid, and linolenic acid. In some embodiments, the backbone structure is first oxidized and than maleated. In some embodiments, the backbone structure is first maleated and then oxidized.

In some embodiments, an oxmal composition is prepared by the process of: (a) maleating a composition comprising one or more hydrocarbon-based backbone structures having at least one site of unsaturation; and (b) oxidizing the composition. In some embodiments, step (a) is performed before step (b), while in other embodiments, step (b) is performed before step (a). In some embodiments, the composition can comprise (i.e. the hydrocarbon-based backbone structures are) fatty acids, rosin acids, distillation products thereof, or mixtures thereof. In some embodiments, the compositions are chosen from tall oil, animal oils, plant oils, algal produced oils, microbial produced oils, distillation products thereof, and mixtures thereof. A person of ordinary skill will appreciate that certain of these oils or products thereof may have to be saponified prior to oxidation and maleation to obtain an appropriate backbone structure, or a fatty acid.

In some embodiments, suitable oils which can be used for preparing an oxidized and maleated composition include without limitation: linseed (flaxseed) oil, castor oil, tung oil, soybean oil, cottonseed oil, olive oil, canola oil, corn oil, sunflower seed oil, coconut oil, rape seed oil, safflower oil, tall oil, palm oil, the distillation products thereof, and mixtures thereof. These oils contain as one constituent linoleic acid, an unsaturated long chain fatty acid as well as other unsaturated fatty acids. In some embodiments, suitable oils include without limitation fish oil, such as herring oil, menhaden oil, and sardine oil.

In the preparation of an oxmal composition, as with the preparation of an oxmal compound, the oxidation and the maleation of the hydrocarbon-backbone structures of the composition can be conducted in either order. For example, a fatty acid composition can first be maleated and then the maleation can be followed by an oxidation (see Example 3 and 4). Alternatively, the fatty acid composition can first be oxidized and then the oxidized composition can be maleated (see Example 1).

In some embodiments, the process of making an oxmal composition comprises oxidizing a commercially available maleated fatty acid composition, such as without limitation XTOL® 690 or XTOL® 692. In some embodiments, the process of making an oxmal composition comprises maleating a commercially available oxidized tall oil composition, such as without limitation XTOL® MTO.

In some embodiments, oxidation is accomplished by heating the compositions containing the hydrocarbon-backbone based structures, such as for example tall oils, in the presence of oxygen or air. Unsaturated hydrocarbon-based structures can be polymerized by heating them in the presence of oxygen or air. This polymerization can cause an increase in the viscosity of the oxmal composition. A catalyst can be used to increase the speed of the oxidation reaction in order to reduce the time required to attain the desired level of oxidation and associated viscosity increase, or to reduce the temperature at which the oxidation is conducted. Use of such a catalyst is optional. In some embodiments, a hydrocarbon-based structure can be a fatty acid, rosin acid, or mixtures thereof. Without being bound by theory, the oxidative heating treatment is believed to cause crosslinking of the hydrocarbon chains acid via their double bonds (sites of unsaturation) and allylic sites, via a direct bond, an ether linkage, or a peroxide linkage. The oxidation treatment is continued until a desired result is obtained, for example, a desired acid value or a desired viscosity.

In some embodiments, the oxidation step in the process of producing an oxmal composition involves oxidizing a tall oil composition by heating the tall oil material to a temperature at least about 150° C., for example to a temperature in the range of about 160° C. to about 170° C., followed by sparging oxygen or air through the heated tall oil composition. As understood by those skilled in the art, a variety of techniques and devices can advantageously be used to inject the oxygen or air into the heated tall oil and the present method is not limited to any specific technique or equipment. As discussed above, the oxidation reaction can be continued until the desired acid value or viscosity is achieved in the tall oil, indicative that the desired level of cross-linking has been obtained in the oxidized tall oil material.

In some embodiments, the maleation step in the process of producing an oxmal composition involves reaction of the hydrocarbon-based structures in the composition with one or more α,β unsaturated carboxylic acids or anhydrides. The amount of α,β unsaturated carboxylic acid or anhydride used varies based on the composition to be maleated. Suitable amounts of the anhydride (or acid(s)) may range from about 2% to about 40% by weight, based on the combined weight of the composition and the anhydride (or acid(s)) and/or the desired amount of maleation. In some embodiments, the amount of anhydride (or acid(s)) can range from about 2% to about 25% by weight, usually from about 2% to about 15% by weight, based on the combined weight of the composition and the anhydride (or acid(s)) and/or the desired amount of maleation. In some embodiments, the α,β unsaturated carboxylic acid or anhydride is chosen from maleic anhydride, fumaric acid, or (meth)acrylic acid. In some embodiments, the α,β unsaturated carboxylic acid or anhydride is a biogenically derived unsaturated carboxylic acid or anhydride. The composition of products prepared is related to the percent maleation performed. Accordingly, in some oxmal compositions, oxmal compounds may include compounds that have been maleated, for example, on at least one hydrocarbon-based backbone structure, at least two hydrocarbon-based backbone structures, on all hydrocarbon-based backbone structures. In certain embodiments, an oxmal composition may further comprise compounds that have been oxidized but have not been maleated.

In contrast to the prior art, where there apparently has been a concerted effort to use tall oil materials containing primarily, if not almost exclusively, tall oil fatty acids (TOFA) and to conduct the maleation reaction (e.g. the reaction with maleic anhydride and/or fumaric acid, and/or acrylic acid), in a way to promote the formation of the Diels-Alder reaction adduct with linoleic acid (generally by using a catalyst), the present inventors have found that such restrictions are not necessary. In some embodiments according to the invention, the conditions under which the maleation reaction proceeds do not need to be controlled (e.g. a catalyst is not needed) such that the Diels-Alder reaction predominates; there is no need to focus on the production of the Diels-Alder reaction adduct with conjugated fatty acids, such as linoleic acid.

For example, the maleation of a tall oil, such as without limitation a crude tall oil or tall oil distillate or component, proceeds by reaction of the tall oil and, for example, one or more of maleic anhydride, fumaric acid, and (meth)acrylic acid. Once combined, the reaction mixture is heated to a temperature of from about 150° C. to about 250° C. In certain embodiments, the reaction temperature is from about 200° C. to about 230° C. In other embodiments, the reaction temperature is from about 215° C. to about 225° C. In some embodiments, a catalyst can be used. Such catalysts are known in the art.

The maleation reaction is essentially complete after a reaction time from about 5 hours to about 36 hours, and typically from about 20 hours to about 30 hours. Without being bound by theory, the maleic anhydride, fumaric acid, and/or (meth)acrylic acid reacts with the hydrocarbon-based material, at the various sites of unsaturation present in the material. For example, the reaction of maleic anhydride with an unsaturated tall oil fatty acid results in the addition of the anhydride ring to the acid at olefinic sites via the so-called "ene" reaction. The reaction of maleic anhydride with a rosin acid derived from tall oil, at diolefinic sites and with conjugated unsaturated fatty acids, may alternatively form a Diels-Alder addition product having a 6-membered ring with one site of unsaturation. Non-limiting examples of representative reactions that can occur are illustrated in U.S. Pat. No. 4,927,669.

A representative set of structures of molecular species potentially found in maleated tall oil compositions (especially tall oil compositions maleated with maleic anhydride) suitable for use as the starting material for making chemically modified oxidized and maleated unsaturated fatty acid compositions include the Diels-Alder reaction product with conjugated linoleic acid and ene reaction products with oleic and elaidic acids as follows:

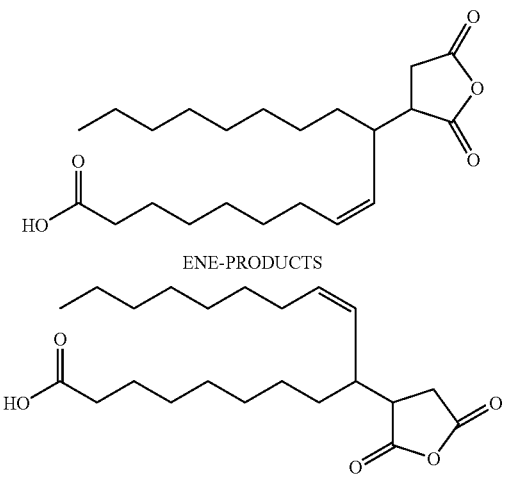

ENE-PRODUCTS

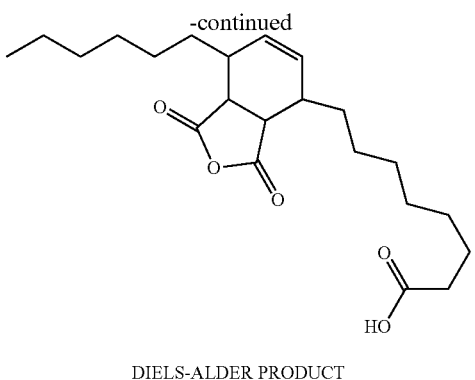

DIELS-ALDER PRODUCT

As will be appreciated by those skilled in the art, certain analogous structures are formed when using any α,β unsaturated carboxylic acid or anhydride for these maleation reactions.

In some embodiments, tall oil distillate components suitable for use in the process of making an oxmal composition include without limitation: fatty acids, tall oil rosin acids, and mixtures of these fractions. The refinement (i.e. fractionation) of tall oil can, for example, provide $C_{16}$-$C_{18}$ saturated and unsaturated fatty acids as well as fatty acid/rosin acid mixtures. In preparing maleated tall oil, such tall oil distillate components, lighter (i.e. lower boiling) or heavier (i.e. higher boiling) components, or components having broader or narrower boiling point ranges may be used in the reaction with an α,β unsaturated carboxylic acid or anhydride. Mixtures or blends of various tall oil distillate fractions may also be employed as the tall oil material. Fatty acid/rosin acid mixtures in a desired ratio may be obtained in a single distillate fraction by adjusting tall oil fractionation conditions. Representative tall oil distillate components include commercially available products XTOL® 100, XTOL® 300, XTOL® 304, and XTOL® 520 (from Georgia-Pacific Chemicals LLC, Atlanta, Ga.).

In one embodiment, for example, a mixture of a first tall oil distillate fraction comprising predominantly tall oil fatty acids (e.g., XTOL® 100) and a second tall oil distillate fraction comprising predominantly rosin acids (e.g., LYTOR® 100) may be blended in a wide range of proportions. In such mixtures, representative amounts of fatty acids and rosin acids range from about 20% to about 99% by weight and from about 1% to about 55% by weight, respectively. Representative weight ratios of the first tall oil distillate fraction to the second tall oil distillate fraction may range from about 3:2 to about 4:1. If such a blend is used to form a maleated tall oil material via reaction with an α,β unsaturated carboxylic acid or anhydride, suitable amounts of the anhydride (or acid(s)) may range from about 2% to about 25% by weight, usually from about 2% to about 15% by weight, based on the combined weight of the tall oil fractions and the anhydride (or acid(s). Depending on the tall oil composition and fractionation conditions, a single tall oil distillate fraction may also suffice to yield a composition that is substantially the same as any of the blends of tall oil distillate fractions discussed above.

In certain embodiments, maleated unsaturated fatty acid compositions suitable for use in making an oxidized and maleated unsaturated fatty acid composition are commercially available. For example, maleated tall oil products can be obtained commercially as XTOL® 690 and XTOL® 692 (from Georgia-Pacific Chemicals LLC, Atlanta, Ga.).

As noted above, the steps of oxidation and maleation of hydrocarbon-based composition can be conducted in either order, as illustrated by the examples which follow.

IV. Methods of Use

Also provided herein are methods of using oxmal compounds and compositions. Such compounds and compositions can be used in a variety of industrial processes. In some methods, compounds and compositions in accordance with some embodiments of the invention can be used as emulsifiers. In some methods, compounds and compositions in accordance with some embodiments of the invention (and mixtures thereof) can be used as corrosion inhibitors.

Certain of the oxmal compositions, compounds, and mixtures thereof described above may be used as emulsifiers. In one embodiment, the compositions can be used in making petroleum-related products, such as invert water-in-oil emulsions used as drilling muds. One standard emulsifier for use in such applications comprises a blend of a primary emulsifier which consists of a carboxylic acid source mixed with an amine source and a secondary emulsifier which is a polyamide based material. In certain embodiments, a solution to be emulsified is combined with an effective amount of an oxmal composition. In some embodiments, an oxmal composition can be used without a nitrogen-containing secondary emulsifier (see Example 5). In some embodiments, an oxmal composition can be used as an emulsifier in oil sand beneficiation.

In alternative embodiments, oxmal composition can be used in an amount of from about 2% to about 15% by weight of the emulsion (e.g., about 2% to about 10%; about 2% to about 8%; about 2% to about 5%; about 2% to about 3%; about 3% to about 15%; about 5% to about 15%; about 8% to about 15%; about 10% to about 15%; about 5% to about 10%; and about 4% to about 12%).

In some embodiments, an oxmal compositions used as an emulsifier can have an acid value between about 65 and 200 mg KOH/g.

In some embodiments, the oxmal composition can be chosen from an oxidized and maleated TOFA composition, an oxidized XTOL® 692 composition, an oxidized XTOL® 690 composition, a maleated XTOL® MTO composition, and mixture thereof.

Some of the oxmal compositions, compounds, and mixtures thereof described above are effective corrosion inhibitors. A method of reducing and/or inhibiting corrosion on a metal surface is provided, the method comprising contacting the metal surface with an effective amount of an oxmal composition, compound, and mixture thereof.

In certain embodiments, oxmal compositions, compounds, and mixtures thereof can be dissolved or dispersed in a carrier solvent to facilitate the coating of metals. Non-limiting examples of carrier solvents include: water, diesel fuels alcohols, kerosene, crude oil and combinations thereof. In some cases, an oxmal composition can be used in a concentration from about 5 ppm up to as much as 10% by weight. In other cases, the composition can be used in an amount between 20 ppm and 1% by weight.

In one embodiment, oxmal compositions, compounds, and mixtures thereof can be used as a corrosion inhibitor in petroleum-recovery applications. In such a case, the downhole conditions in an oil or gas well can vary greatly from one well to the next. For instance, in one environment one may encounter "sweet" conditions (predominately $CO_2$), while in another environment "sour" conditions may predominate ($H_2S$ present). As shown in Example 6, an oxmal composition as described previously, such as in particular an oxidized and maleated tall oil composition is suitable for retarding corrosion in both environments.

In some embodiments, the oxmal composition can be chosen from an oxidized and maleated TOFA composition, an oxidized XTOL® 692 composition, an oxidized XTOL® 690 composition, a maleated XTOL® MTO composition, and mixtures thereof.

In certain embodiments, when utilized in corrosion or emulsion applications, the oxmal composition, compound, and mixtures thereof can be combined with other materials such as alkyleneamines, including diethylenetriamine, imidazoline, amidoamine, amidoamine condensates, alkanolamines and the like.

Oxmal compounds have increased functionality and molecular weight as compared to the hydrocarbon-based starting materials used to produce them. For example, oxmal compositions and compounds have increased acid functionalities available, as compared to their backbone compounds (for example the backbone hydrocarbons, fatty acids or rosin acids) following oxidation and maleation. Such groups can facilitate certain embodiments in their use in various applications including, for example, as emulsifiers and corrosion inhibitors. In one example, the increased acid functionality can increase the utility of oxmal compositions, compounds, and mixtures thereof as corrosion inhibitors by providing more available sites to associate with the metal surface and retard loss of the inhibitor from the surface over time. In addition, when the acid functionalities are in the anhydride state, for example a tall oil composition or compound maleated with maleic anhydride, the anhydride moieties can function additionally to remove water in oil-based applications. In some cases, the increase in molecular weight provides an oxmal composition or compound with increased viscosity and increased stability when compared to the composition's lower molecular weight starting materials.

The applicability of various oxmal compounds and compositions to various of the methods of use may depend, for example, on their acid value, the degree of functionality, molecular weight, and chain length. In some embodiments, a shorter chain length is beneficial, while in other embodiments, a longer chain length is preferred. It is well within the skill of one of the art to produce the appropriate oxmal composition based on the specific characteristics of any application.

EXAMPLES

General Methods

Acid value was determined using standard methods ASTM D 465-05 and AOCS Te 1a-64. Standard test methods ASTM D 803-03 and AOCS Ja 10-87 (93) were used to measure Brookfield viscosity. Gardner-Holdt viscosity was determined using standard methods ASTM D1545-07 and AOCS Ja 11-87 (93). TOF MS data was generated on a JEOL Accu TOF JMS 100 LC Time Of Flight Mass Spectrometer in a negative ion electrospray mode. A 0.05 g of sample was dissolved in 5.0 mL of FIM-FA solvent (1:1:1 methanol: diethyl ether:toluene) and then introduced to the TOF MS.

$^{13}$C NMR data were generated on a Bruker 250 MHz Nuclear Magnetic Resonance Spectrometer. The samples were dissolved in $CDCl_3$ which was also used as the internal lock.

Example 1

Oxidation of Maleated Tall Oil Products

Two maleated tall oil products, XTOL® 690 and XTOL® 692, were oxidized using air at an elevated temperature. XTOL® 690 is a tall oil blend of tall oil fatty acid bottoms and a distilled tall oil, which blend has been maleated at a level of about 3.5%. XTOL® 692 is a blend of a tall oil rosin and tall oil fatty acid, which blend has been maleated at a level of about 12%.

Each of these tall oil blends was charged into a reactor which was fitted with an agitator, a thermocouple and a fritted glass sparge stone attached by a hose to an air supply. The tall oil blends were heated to 165° C. and the air turned on and adjusted to a flow rate of 4 L/hr through the sparge stone. The maleated tall oil reaction mixture was then heated to 177° C. and sampled frequently for acid value and viscosity (Gardner-Holdt) as the oxidation reactions proceeded, while holding the reaction mixture at a temperature of 177° C. The reaction mixture was held at a temperature of 177° C. for 10.5-16 hours as air was sparged. The reaction mixture was then cooled to 70-85° C. and discharged. The final physical properties of the maleated and oxidized tall oil product were determined as described above. TOF MS data is shown in FIG. 2 and $^{13}$C NMR spectra are illustrated in FIGS. 3 and 5. The properties of the maleated and oxidized tall oil products were measured as shown in the following table with reference to typical properties of the starting materials:

|  | XTOL® 690 | Oxidized XTOL® 690 | XTOL® 692 | Oxidized XTOL® 692 |
|---|---|---|---|---|
| Acid Value (mg KOH/g) | 197.3 | 158.7 | 276.0 | 203.9 |
| Brookfield Viscosity (cPs; 25° C.) | 484.9 | 8496 | 1451 | 18010 |
| Density (Lbs./gal) | 8.00 | 8.38 | 8.41 | 8.59 |
| Sp. Gravity (25° C.) | 0.961 | 1.006 | 1.010 | 1.031 |

| | | Visc (cPs; | GPC Results | | | | | |
| | | | UV Detector | | | RI Detector | | |
| Description | AcV | 25° C.) | Mn | Mw | Mz | Mn | Mw | Mz |
|---|---|---|---|---|---|---|---|---|
| Oxidized XTOL® 692 | 210.4 | 13560 | 654 | 1421 | 2884 | 519 | 844 | 1900 |
| Oxidized XTOL® 690 | 158.7 | 8970 | 800 | 3410 | 9378 | 618 | 1959 | 7330 |

Example 2

Maleation of Oxidized Tall Oil

An oxidized and maleated tall oil composition was produced through the maleation of a commercially available oxidized tall oil product. The oxidized tall oil product, XTOL® MTO, which is an oxidized, high acid value crude tall oil, available commercially from Georgia Pacific was used as the starting material. This oxidized crude tall oil was treated with maleic anhydride.

XTOL® MTO (95 wt %) was charged to a sealed reactor fitted with an agitator, a thermocouple and a condenser. The reactor was heated to 180° C. At 180° C. maleic anhydride (5 wt %) was added slowly to the reactor. The reaction mixture was then heated to 200° C. for approximately 3-6 hours or until all of the maleic anhydride had reacted. The reaction mixture was then cooled to 70-80° C. and discharged. The final physical properties were determined as described above. A $^{13}$C NMR spectrum is shown in FIG. 6. The properties of the oxidized and maleated tall oil product were measured as shown in the following table with reference to typical properties of the starting materials:

|  | XTOL ® MTO | Maleated XTOL ® MTO (Oxidized tall oil) |
| --- | --- | --- |
| Acid Value | 143.0 | 163.8 |
| Density (25° C.; Lbs./gal) | 8.25 | 8.52 |
| Sp. Gravity (25° C.) | 0.99 | 1.023 |
| Brookfield Viscosity (cPs: 25° C.) | 4870 | 22580 |

Example 3

Maleation of Crude Tall Oil Followed by Oxidation

A process similar to the one described in Example 1 was used, whereby a crude tall oil mixture was maleated followed by oxidation. In this specific example, the composition was maleated to a level of about 5% and then oxidized.

A crude tall oil (95 wt. %) was charged to a sealed reactor fitted with an agitator, a thermocouple, and a condenser. The reaction mixture was heated to 180° C. At 180° C., maleic anhydride (5 wt. %) was added slowly to the reactor. The reaction mixture was then heated to 200° C. for approximately 3-6 hours or until all of the maleic anhydride had reacted. Once all of the maleic anhydride had reacted, the reaction mixture was then cooled to 180° C. and air was introduced to the reaction mixture using a fritted glass sparge stone attached by a hose to an air supply. The air was turned on and adjusted to a flow rate of 4 L/hr through the sparge stone. Oxidation of the maleated crude tall oil with air was carried out for 12-16 hours. The reaction mixture was then cooled to 70-85° C. and discharged. The final physical properties were determined. The properties of the maleated and oxidized tall oil product were measured as shown in the following table with reference to typical properties of the starting materials:

|  | Crude Tall Oil | Maleated-Oxidized Crude tall oil |
| --- | --- | --- |
| Acid Value | 161.6 | 169.5 |
| Density (25° C.; Lbs/gal) | 8.088 | 8.54 |
| Specific Gravity (25° C.) | 0.9706 | 1.027 |
| Brookfield Viscosity (cPs; 25° C.) | 695.0 | 33800 |

Example 4

Oxidation of Maleated Tall Oil Fatty Acid

In this example, a maleated tall oil fatty acid (TOFA) was oxidized using air at an elevated temperature.

TOFA was charged to a sealed reactor and the contents of the reactor were heated to 70° C. Once a temperature of 70° C. was achieved, maleic anhydride in an amount of about 25% by weight of the overall reaction was added to the vessel. The reactor mixture was then heated to 220° C. in several stages. From the starting temperature of 70° C., the temperature was increased in small increments until 220° C. was achieved. After each temperature adjustment and the desired set point was reached, the material was maintained at the set point temperature for a five minute hold period. The first stage of heating was from 70° C. to 130° C.; the second stage of heating was from 130° C. to 160° C.; the third stage of heating was from 160° C. to 185° C.; the fourth stage of heating was from 185° C. to 205° C.; and the fifth and final stage of heating was from 205° C. to 220° C. The reaction mixture then was held at 220° C. until a Gardner-Holdt viscosity of about Z-2 was reached. This holding period typically required about 5 hours depending on the batch size. The reaction mixture was cooled to a discharge temperature and the physical properties of the maleated product were measured as described above. Typically, the maleated product exhibited an acid number (hydrous) equal to 300-320 mg KOH/g, a specific gravity of 1.04 and a Brookfield Viscosity (at 25° C.) equal to 2700-3400 cps.

To produce a maleated and oxidized fatty acid composition, the maleated tall oil fatty acid was then charged to a reactor which was fitted with an agitator, a thermocouple, and a fritted glass sparge stone attached by a hose to an air supply. The maleated tall oil fatty acid was heated to 165° C. and the air was turned on and adjusted to a flow rate of 4 L/hr through the sparge stone. The reaction mixture was then heated to 177° C. and sampled frequently for acid value and viscosity (Gardner-Holdt) while holding the reaction mixture at 177° C. The reaction mixture was held at 177° C. for 10.5-16 hours as air was sparged. The reaction mixture was then cooled to 70-85° C. and discharged. The final physical properties of the maleated and oxidized TOFA were then determined as described above. TOF MS data is shown in FIG. 1 and a $^{13}$C NMR spectrum is illustrated in FIG. 4. The properties of the maleated and oxidized TOFA were measured as:

|  | Oxidized Maleated Tall Oil Fatty Acid |
| --- | --- |
| Acid Value | 250 |
| Density (25° C.; Lbs./gal) | 8.80 |
| Specific Gravity (25° C.) | 1.056 |
| Brookfield Viscosity (cPs; 25° C.) | 17530 |

|  |  | Visc | GPC Results | | | | | |
| --- | --- | --- | --- | --- | --- | --- | --- | --- |
|  |  |  | UV Detector | | | RI Detector | | |
|  |  | (cPs; | | | | | | |
| Description | AcV | 25 C.) | Mn | Mw | Mz | Mn | Mw | Mz |
| Oxidized Maleated TOFA | 258.5 | 13560 | 830 | 1503 | 2678 | 654 | 908 | 1603 |
| Oxidized Maleated TOFA | 247.3 | 19328 | 841 | 1535 | 2759 | 644 | 879 | 1548 |

Example 5

Emulsification

Several oxidized and maleated tall oil products were examined for their ability to produce oil well mud without the use of a nitrogen-containing secondary emulsifier. One standard emulsifier comprises a blend of a primary emulsifier which consists of a carboxylic acid source mixed with an amine source and a secondary emulsifier which is a polyamide based material. The results presented in the table below indicate that acceptable emulsification was achieved using only a single emulsifier. For purpose of comparison, proprietary tests examining fluid loss values (FL) and the electrical stability (ES) of various samples were conducted using the API Recommended Practice Standard Procedure for Field Testing of Oil-Based Drilling Fluids, 13B-2, $3^{rd}$ Ed., 1998. The fluid loss values (FL) were much lower compared to the industry standard emulsifier package and the electrical stability was fairly high. This suggests that lower cost, more environmentally-friendly emulsifiers may be made using the oxidized and maleated compositions provided herein.

|  | Standard Emulsifier | Maleated TOFA | Oxidized XTOL ® 690 | | Oxidized Maleated TOFA | | Maleated MTO | | Oxidized XTOL ® 692 |
| --- | --- | --- | --- | --- | --- | --- | --- | --- | --- |
| Conc. (ppb) | 9 | 9 | 9 | 9 | 9 | 9 | 9 | 9 | 9 |
| ES | 787 | 499 | 549 | 536 | 647 | 678 | 448 | 565 | 644 |
| FL (mLs) | 6.6 | 6.0 | 3.2 | 3.4 | 11.6 | 3.2 | 3.6 | 2.5 | 3.4 |

Example 6

Corrosion Inhibition

Maleated and oxidized tall oil compositions were also tested as corrosion inhibitor formulations under both sweet gas (no $H_2S$ present) and sour gas ($H_2S$ present) conditions. Sweet gas-corrosion tests were conducted under the following conditions: Brine composition: 3.3% NaCl and 1.2% $CaCl_2$; Ratio: 80% brine and 20% deodorized kerosene (air blown); Gas-saturated $CO_2$; Temperature: 160° F. (71° C.); Time: 72 hours. The results of the sweet gas tests are listed in the table below. The amine used in all of the tests was tall oil-based imidazoline. The samples were evaluated using the Wheel Test Method for Evaluation of Film-Persistent Corrosion Inhibitors for Oilfield Applications, Item No. 24007, NACE International Publication 1D182 (2006 Edition).

| | % Protection | | |
| --- | --- | --- | --- |
| Samples | 5 ppm | 10 ppm | 20 ppm |
| Control A | 79 | 92 | 96 |
| Amine + Oxidized and Maleated TOFA | 96 | 97 | 97 |
| Amine + Oxidized XTOL ® 692 | 90 | 90 | 92 |
| Control B | 90 | 93 | 96 |
| Amine + Maleated TOFA | 98 | 99 | 87 |
| Control C | 64 | 88 | 88 |
| Amine + Oxidized XTOL ® 692 | 79 | 86 | 93 |
| Amine + Maleated MTO | 85 | 84 | 88 |

The method described above was also used for sour gas test conditions, with the exception that $H_2S$ was added to the test gas. The results are shown in the following table. In this case, the control was an amine (DETA/Imidazoline) neutralized TOFA.

| Coupon | Wt. Loss (mg) | % Protection | Mils/Year | Sample @ ppm |
| --- | --- | --- | --- | --- |
| 1 | 7.1 | 80.8 | 30.7 | Maleated TOFA @ 2500 |
| 3 | 3.3 | 91.1 | 14.2 | Maleated TOFA @ 5000 |
| 5 | 8.2 | 77.8 | 35.4 | Oxidized XTOL ® 690 @ 2500 |
| 7 | 4.2 | 88.6 | 18.1 | Oxidized XTOL ® 690 @ 5000 |
| 9 | 6.3 | 83.0 | 27.2 | Oxidized XTOL ® 692 @ 2500 |
| 11 | 3.0 | 91.9 | 13.0 | Oxidized XTOL ® 692 @ 5000 |
| 13 | 6.4 | 82.7 | 27.6 | Maleated MTO @ 2500 |
| 15 | 2.9 | 92.2 | 12.5 | Maleated MTO @ 5000 |
| 17 | 5.6 | 84.9 | 24.2 | Oxidized and Maleated TOFA @ 2500 |
| 19 | 4.4 | 88.1 | 19.0 | Oxidized and Maleated TOFA @ 5000 |
| 21 | 4.7 | 87.3 | 20.3 | Control @ 2500 |
| 23 | 4.0 | 89.2 | 17.3 | Control @ 5000 |
| 25 | 40.6 | 0 | 175.3 | Blank |
| 26 | 41.7 | 0 | 180.0 | Blank |

The results of the corrosion testing indicate that these products generally performed better than the standards used for comparison. That is, the formulations which contain an oxidized and maleated tall oil composition typically showed a higher level of protection compared to the control. In addition, the sour gas testing was performed under conditions which did not use an amine neutralization. Therefore, the oxidized and maleated compositions provided herein demonstrated excellent corrosion inhibition while not having to use amines in the formulation which may be of an environmental and economic advantage.

Example 7

Oxidation of Maleated Arachidonic Acid (ARA)

In this example, a maleated arachidonic acid (ARA) is oxidized using air at an elevated temperature. Arachidonic acid is produced by the saponification of natural fish oils and is particularly prevalent in sardine oil.

ARA is charged to a sealed reactor and the contents of the reactor are heated to 70° C. Once a temperature of 70° C. is achieved, maleic anhydride in an amount of about 40% by weight of the total reaction is added to the vessel. The reactor mixture is then heated to 220° C. in several stages. From the starting temperature of 70° C., the temperature is increased in small increments until 220° C. is achieved. After each temperature adjustment and the desired set point is reached, the material is maintained at the set point temperature for a five minute hold period. The first stage of heating is from 70° C. to 130° C.; the second stage of heating is from 130° C. to 160° C.; the third stage of heating is from 160° C. to 185° C.; the fourth stage of heating is from 185° C. to 205° C.; and the fifth and final stage of heating is from 205° C. to 220° C. The reaction mixture then is held at 220° C. until a Gardner-Holdt viscosity of about Z-2 is reached. This holding period varies depending on the batch size. The reaction mixture is cooled to a discharge temperature and the physical properties of the maleated product are measured as described in previous examples.

To produce a maleated and oxidized ARA composition, the maleated ARA is then charged to a reactor which is fitted with an agitator, a thermocouple, and a fritted glass sparge stone attached by a hose to an air supply. The maleated ARA is heated to 165° C. and the air is turned on and adjusted to a flow rate of 4 L/hr through the sparge stone. The reaction mixture is then heated to 177° C. and sampled frequently for the acid value and viscosity (Gardner-Holdt) that is appropriate for the specific application while holding the reaction mixture at 177° C. The reaction mixture is held at 177° C. for the length of time necessary to achieve the desired acid value and viscosity as air is sparged. The reaction mixture is then cooled to 70-85° C. and discharged.

A non-limiting example of a compound produced by the above procedure is:

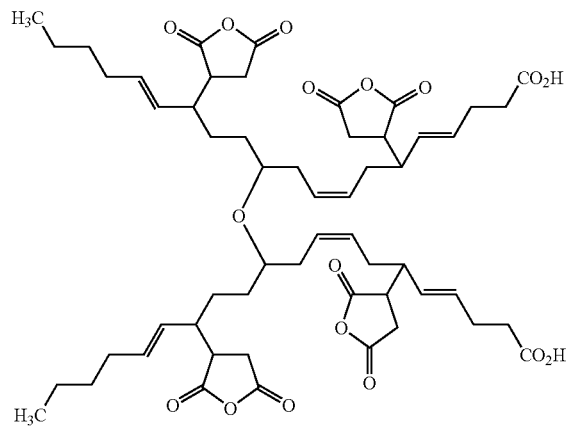

A number of embodiments have been described. Nevertheless, it will be understood that various modifications may be made without departing from the spirit and scope of the disclosure. Accordingly, other embodiments are within the scope of the following claims.

What is claimed is:
1. An oxidized and maleated composition, comprising:
one or more compounds or salts thereof having at least two $C_{10}$-$C_{24}$ structures, wherein at least one of the $C_{10}$-$C_{24}$ structures is substituted by at least one of an α,β unsaturated carboxylic acid or anhydride,
wherein the $C_{10}$-$C_{24}$ structures are crosslinked by an ether linkage, and
wherein the composition is an oxidized and maleated tall oil composition.

2. An oxidized and maleated composition, comprising:
one or more compounds or salts thereof having at least two $C_{10}$-$C_{24}$ structures, wherein at least one of the $C_{10}$-$C_{24}$ structures is substituted by at least one of an α,β unsaturated carboxylic acid or anhydride,
wherein the $C_{10}$-$C_{24}$ structures are crosslinked by an ether linkage, and
wherein the oxidized and maleated tall oil composition is selected from crude tall oil; tall oil fatty acid; and tall oil distillation bottoms.

3. A tall oil composition comprising a tall oil fatty acid having at least three acid functionalities, wherein the tall oil composition has a tall oil fatty acids crosslinked between hydrocarbon chains by an ether linkage.

4. The tall oil composition according to claim 3, wherein the composition further comprises compounds having at least six acid functionalities.

5. The tall oil composition according to claim 3, wherein the composition further comprises one or more oxidized and maleated fatty acids, rosin acids, or combinations thereof.

6. The tall oil composition according to claim 3, wherein the composition further comprises one or more of free fatty acid, rosin acid, maleated but not oxidized fatty acid, maleated but not oxidized rosin acid, oxidized but not maleated fatty acid, oxidized but not maleated rosin acid, oxidized and partially maleated fatty acid, and oxidized and partially maleated rosin acid.

7. The tall oil composition according to claim 3, further comprising one or more of the following:

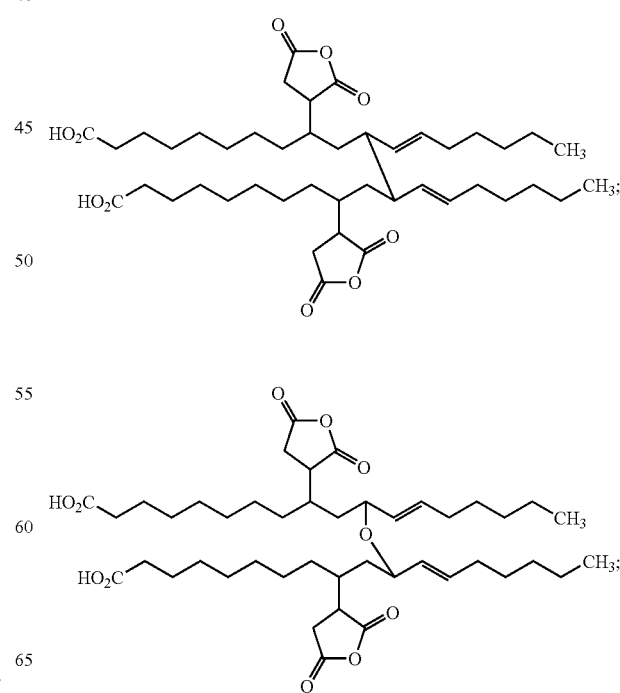

63
-continued
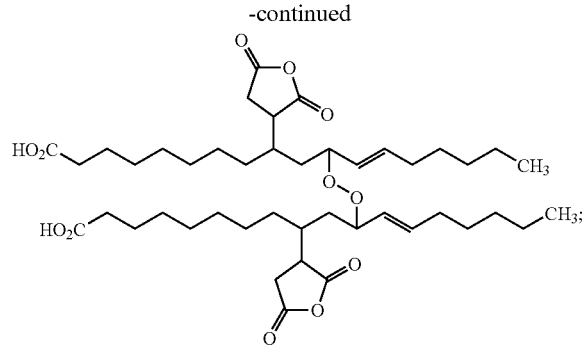
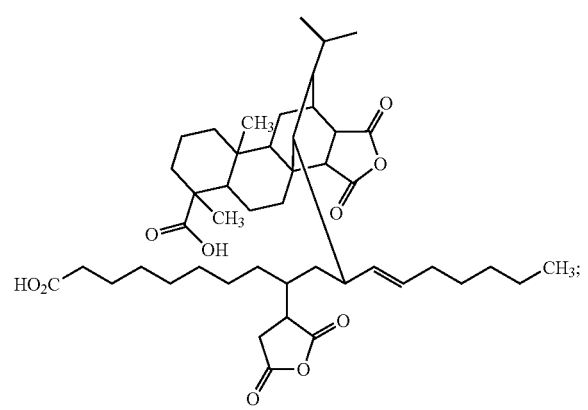
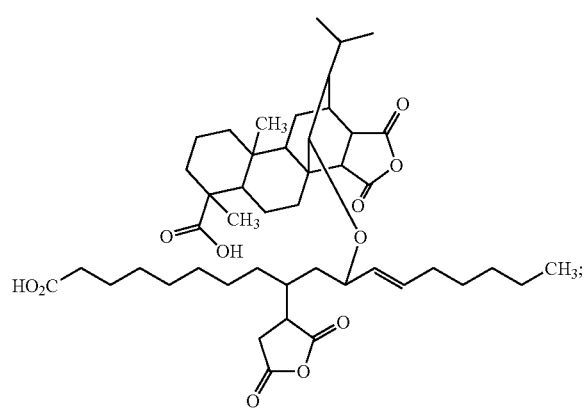
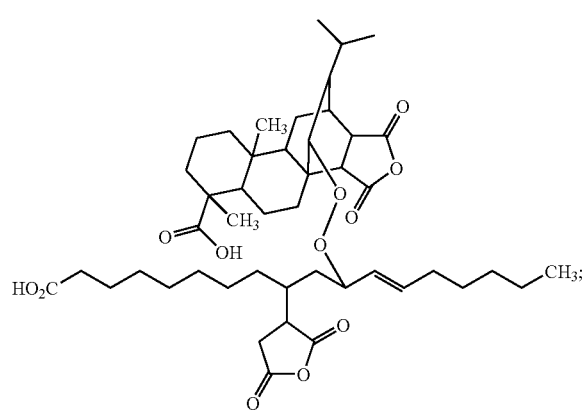
64
-continued
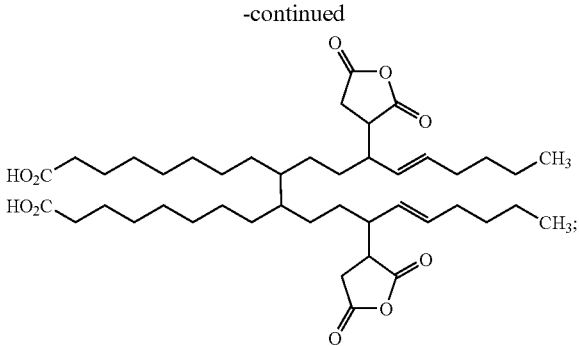
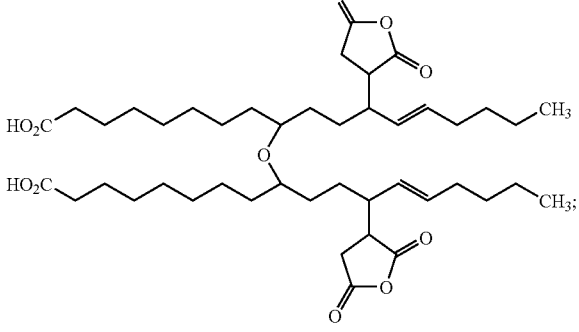
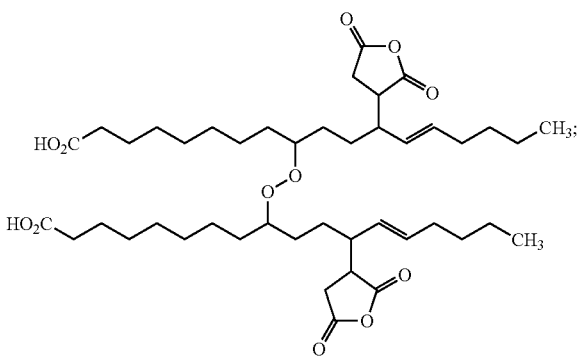
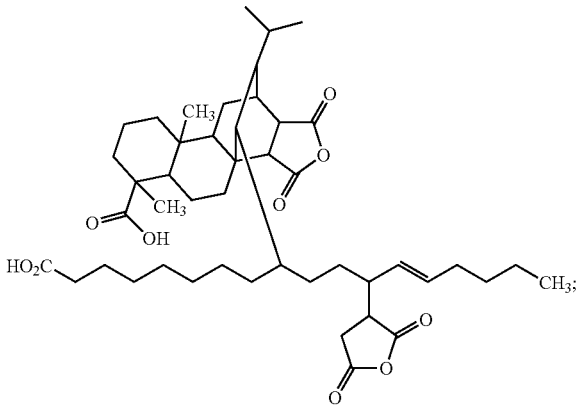

65                                    66

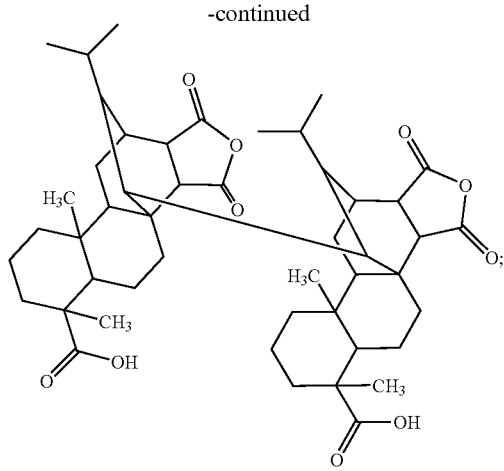
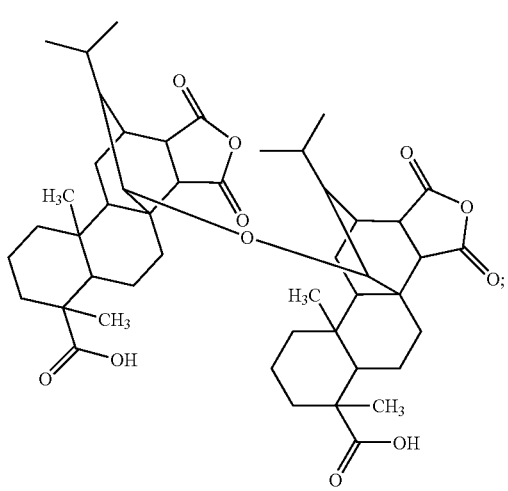
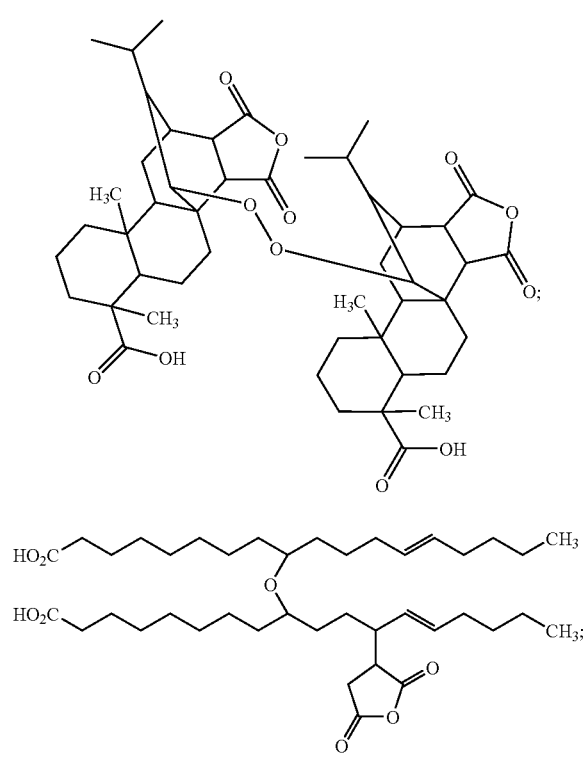
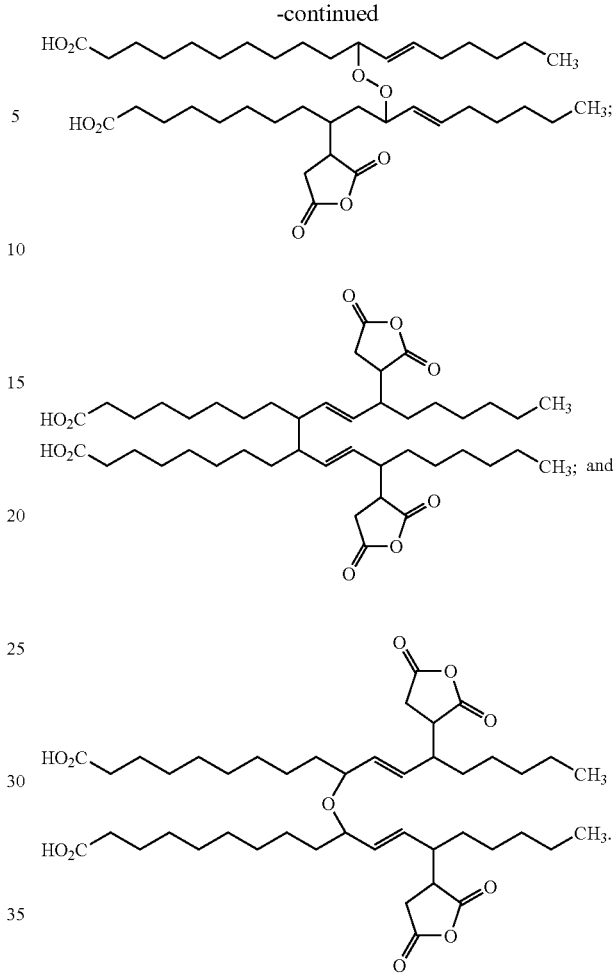
8. The composition according to claim 3, wherein the composition further comprises one or more of the following:

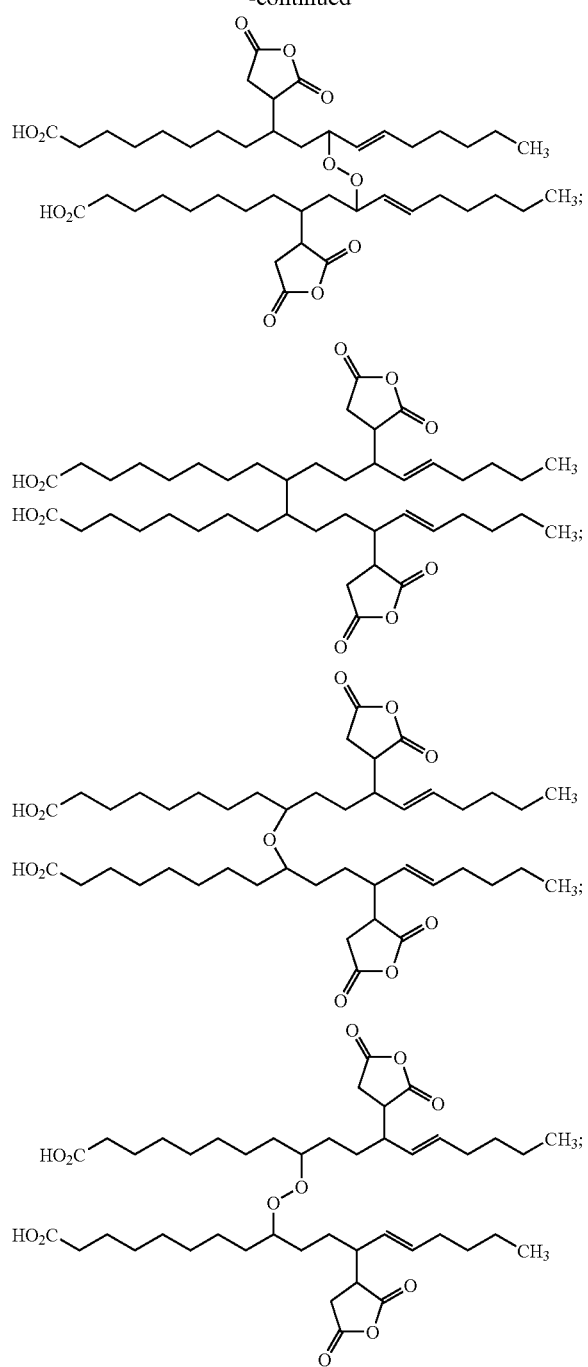
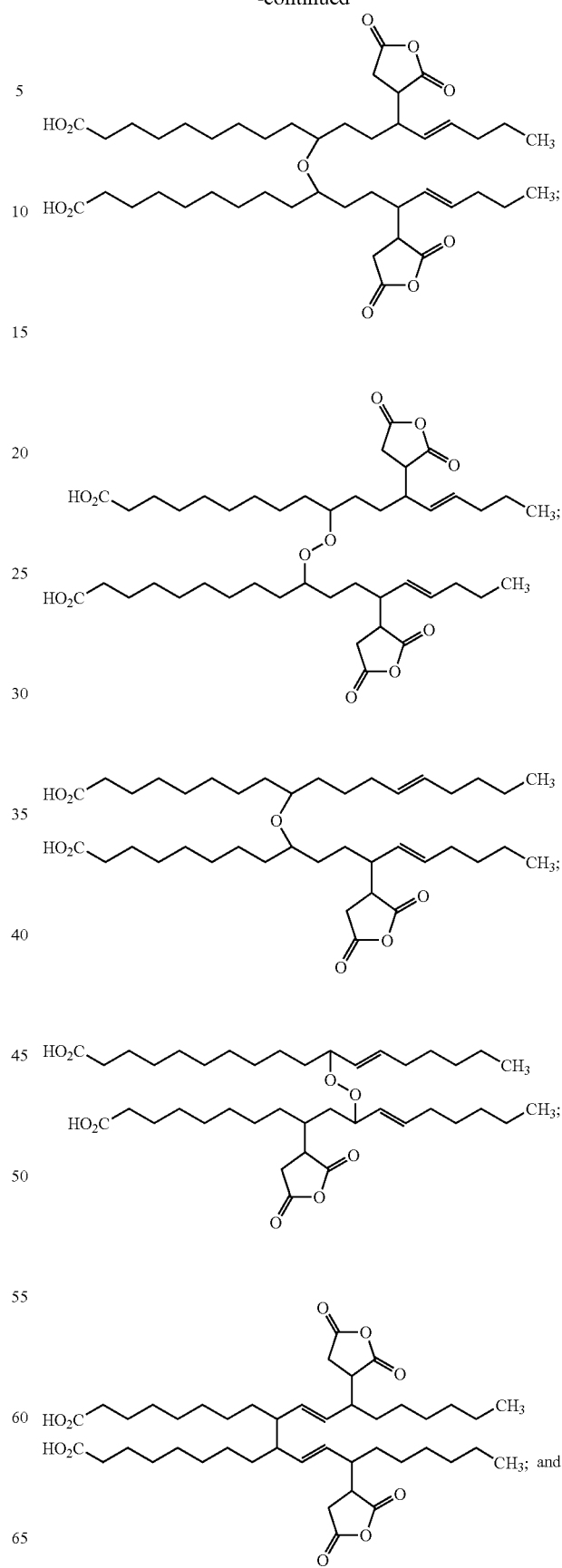

-continued

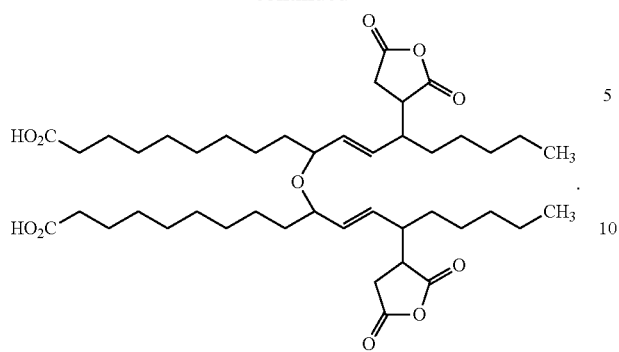

9. A method for making an oxmal composition comprising:

maleating a composition comprising at least two $C_{10}$-$C_{24}$ structures, wherein at least one of the structures has at least one site of unsaturation; and oxidizing the composition to provide an ether linkage between the at least two $C_{10}$-$C_{24}$ structures, wherein the composition is selected from crude tall oil; tall oil fatty acid; and tall oil distillation bottoms.

10. A method for making an oxmal composition comprising:

maleating a composition comprising at least two $C_{10}$-$C_{24}$ structures, wherein at least one of the structures has at least one site of unsaturation; and oxidizing the composition to provide an ether linkage between the at least two $C_{10}$-$C_{24}$ structures, wherein the composition comprises a tall oil fatty acid.

* * * * *